(12) United States Patent
Anderson et al.

(10) Patent No.: US 8,513,205 B2
(45) Date of Patent: Aug. 20, 2013

(54) POTENT CHIMERIC NRTI-NNRTI BIFUNCTIONAL INHIBITORS OF HIV-1 REVERSE TRANSCRIPTASE

(75) Inventors: Karen S. Anderson, Guilford, CT (US); Roger Hunter, Cape Town (ZA)

(73) Assignees: Yale University, New Haven, CT (US); University of Cape Town, Cape Town (ZA)

( * ) Notice: Subject to any disclaimer, the term of this patent is extended or adjusted under 35 U.S.C. 154(b) by 298 days.

(21) Appl. No.: 12/933,757

(22) PCT Filed: Apr. 9, 2009

(86) PCT No.: PCT/US2009/002226
§ 371 (c)(1),
(2), (4) Date: Dec. 15, 2010

(87) PCT Pub. No.: WO2009/126293
PCT Pub. Date: Oct. 15, 2009

(65) Prior Publication Data
US 2011/0312880 A1    Dec. 22, 2011

Related U.S. Application Data

(60) Provisional application No. 61/123,768, filed on Apr. 11, 2008.

(51) Int. Cl.
*A01N 43/04*    (2006.01)
*A61K 31/70*    (2006.01)
(52) U.S. Cl.
USPC ............... 514/43; 514/45; 514/46; 514/47; 514/48; 514/49; 514/50; 514/51
(58) Field of Classification Search
None
See application file for complete search history.

(56) References Cited

PUBLICATIONS

Petersen et al. J. Med. Chem. (2005), vol. 48, pp. 1211-1220.*
Corbett JW et al., Inhibition of Clinically Relevant Mutant Variants of HIV-1 by Quinazolinone Non-Nucleoside Reverse Transcriptase Inhibitors. J. Med. Chem. 2000, 43, 2019-2030.
Fisac C et al, Metabolic benefits 24 months after replacing a protease inhibitor with abacavir, efavirenz or nevirapine. AIDS 2005, 19(9), 917-925.
Gulick RM et al., Triple-Nucleoside Regimens versus Efavirenz-Containing Regimens for the Initial Treatment of HIV-1 Infection. The New England Journal of Medicine Apr. 29, 2004, 350, 1850-1861.

* cited by examiner

*Primary Examiner* — Patrick Lewis
(74) *Attorney, Agent, or Firm* — Henry D. Coleman; R. Neil Sudol

(57) ABSTRACT

The present invention relates to compounds, in particular, dual antagonists comprising a nucleoside reverse transcriptase inhibitor (NRTI) or a nucleoside competitive reverse transcriptase inhibitor and a non-nucleoside reverse transcriptase inhibitor (NNRTI), linked together using a chemical linker, which may be used to inhibit HIV (HIV-1) reverse transcriptase and in the treatment of HIV infections, more severe cases of HIV infections, including ARC and AIDS, including reducing the likelihood of these infections and disease states.

-continued
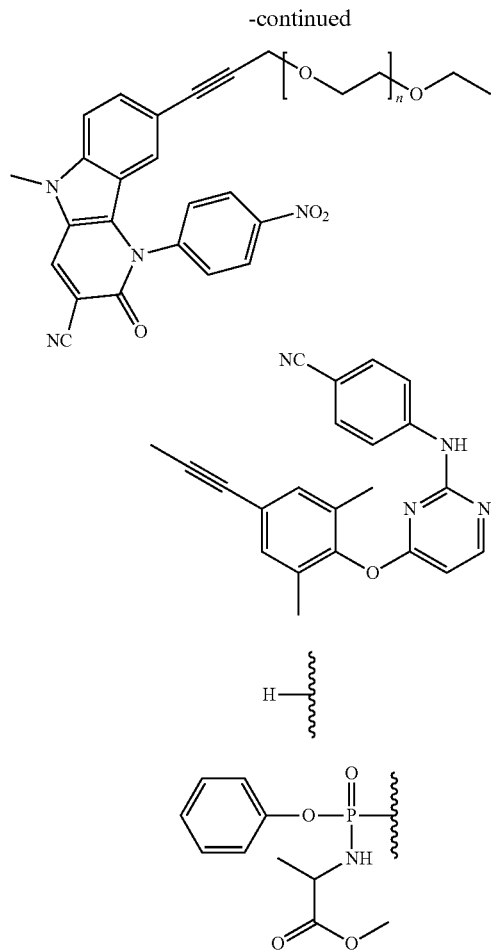
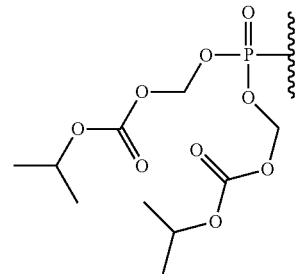
R$_3$
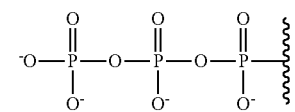
R$_4$
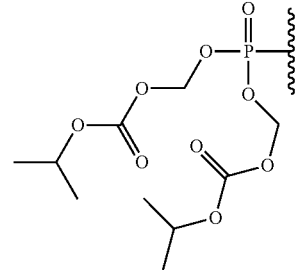
R$_1$
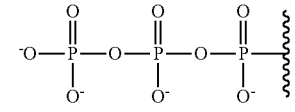
R$_2$
33 Claims, 9 Drawing Sheets

APPROVED NUCLEOSIDE REVERSE TRANSCRIPTASE INHIBITORS

4'-ethynyl D4T (4'ED4T) and 4'-ethynyl-2-fluoro-2'-deoxyadeonsine (4'EFdA)

APPROVED NON-NUCLEOSIDE REVERSE TRANSCRIPTASE INHIBITORS

Representative Bifunctional Compounds

Synthesis of Compounds of Figure 5

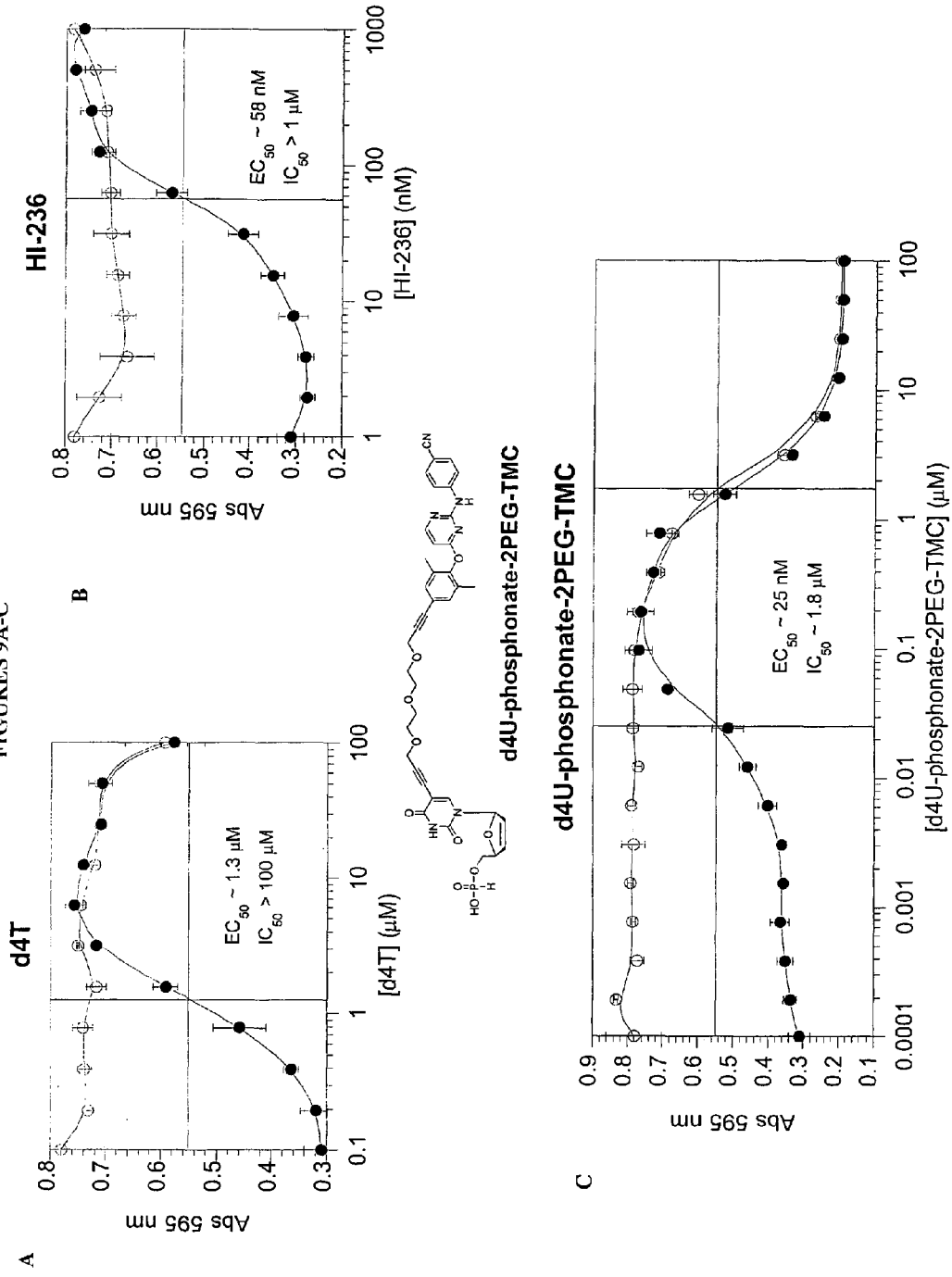
FIGURES 9A-C

POTENT CHIMERIC NRTI-NNRTI BIFUNCTIONAL INHIBITORS OF HIV-1 REVERSE TRANSCRIPTASE

RELATED APPLICATIONS AND GOVERNMENT SUPPORT

This application is a United States national stage of International Patent Application No. PCT/US2009/002226, International Filing Date Apr. 9, 2009, which is an application claiming the benefit of U.S. Provisional Patent Application No. 61/123,768, Filing Date Apr. 11, 2008. The latter two applications are incorporated by reference in their entirety into the United States national stage application.

This invention was made with government support under GM049551 awarded by National Institute of Health. The government has certain rights in the invention.

FIELD OF THE INVENTION

The present invention relates to compounds, in particular, dual antagonists comprising a nucleoside reverse transcriptase inhibitor (NRTI) or a nucleoside competitive reverse transcriptase inhibitor and a non-nucleoside reverse transcriptase inhibitor (NNRTI), linked together using a chemical linker, which may be used to inhibit HIV (HIV-1) reverse transcriptase and in the treatment of HIV infections, more severe cases of HIV infections, including ARC and AIDS, including reducing the likelihood of these infections and disease states. Pharmaceutical compositions based upon these novel compounds are also described.

BACKGROUND OF THE INVENTION

Human Immunodeficiency Virus (HIV-1) is a member of the retroviral family which contains a single-stranded RNA genome and is considered the major etiological agent involved in the development of acquired immunodeficiency syndrome or AIDS. The World Health Organization estimates that as of the end of 2007 over 42 million people worldwide are infected and this number is growing. There continues to be a significant need for new drugs and drug combinations to combat this disease. There are a number of potential steps in the life cycle of the HIV virus for intervention with potential therapeutics. [1] A great deal of effort to develop drugs against HIV has been centered around HIV reverse transcriptase (RT), HIV protease, and more recently viral entry. The drugs that target HIV RT are divided into two general classes classes: nucleoside inhibitors (NRTIs) and non-nucleoside inhibitors (NNRTIs). The NRTI and NNRTI drugs currently approved by the FDA are summarized in FIGS. 3 & 4. [2-12]

The fully functional HIV reverse transcriptase has been shown to be a heterodimer containing two subunits-p66 and p51. Several structures are now available. The most recent ones are the 3-dimensional structure of HIV-1 RT-template/primer-dNTP poised for catalysis [13-16]. These structures will help guide our mechanistic and inhibitor design studies and help corroborate our functional studies. The structure of the HIV-1 RT catalytic complex is shown in FIG. 1. The overall topology of the p66 subunit has been described as a right hand containing fingers, palm, and thumb domains in addition to a connection domain and the RNAseH domain. The polymerase active site lies in the palm of the hand which contains three acidic residues considered to be essential catalytic residues (D185, D186, and D110) based upon mutagenesis studies [17, 18]. In addition there is a connection domain that joins the carboxyl terminal domain (which contains the RNAse H cleavage site) to the right hand. The p51 subunit although completely homologous in sequence to the p66 subunit is strikingly different in structure. The DNA binds along a groove, stretching from the polymerase active site to the RNAseH active site. The DNA has an A-like conformation in the polymerase active site and transitions to a B-like structure 4-5 base pairs away from the active site. The A- to B-form transition in the DNA structure is accompanied by an overall bend of about 40° as previously observed [15]. The NRTI and NNRTI binding sites are noted.

Studies have allowed the present inventors to develop the kinetic model shown in Scheme 1 (FIG. 2) describing the mechanism of polymerization for HIV RT. This is an ordered mechanism with the DNA binding first followed by the nucleotide. The DNA, containing a specified number of bases ($DNA_n$), binds tightly to the RT forming an E•DNA complex that is slow to dissociate. The binding of the dNTP follows. A two step binding process of the dNTP controls the selectivity involved in incorporating the correct nucleotide. The dNTP first binds to the E•$DNA_n$ complex in a loose conformational state that is largely controlled by the base-pairing free energy upon recognition of the correct dNTP over the incorrect dNTP [19]. The binding of the correct dNTP induces a rate-limiting protein conformational change designated by E*•$DNA_n$•dNTP. The formation of this tight ternary complex allows the critical transition state to be reached leading to very rapid chemistry to produce the elongated $DNA_{n+1}$. After nucleotide incorporation, the enzyme must return to the loose state in order to release the $PP_i$ and a translocation step to allow the next round of reaction [20-22]. Additional evidence for the two conformational states of the ternary enzyme, DNA, dNTP complex are provided by the kinetic studies with non-nucleoside inhibitors [23, 24]. The most recent crystal structures nicely corroborate the inventors' initial kinetic model. The rate-limiting conformational state of the protein induced by the binding of the correct dNTP was visualized in the structure of the catalytic complex by the fingers domain closing in toward the palm domain to form a very tight enzyme*-DNA-dNTP complex [14].

The NNRTI class of inhibitors of HIV-1 RT bear no structural resemblance to the nucleosides. Structures of some of the clinically significant non-nucleoside analogs are shown in FIG. 4. Structures of some of the clinically significant nucleoside analogs are shown in FIG. 3. Many types of structurally diverse compounds have been shown to be very potent and selective inhibitors of RT [25]. The 3-dimensional structures of a number of these analogs bound to the RT enzyme have shown that they bind in a hydrophobic pocket proximal to the active site [25]. The structural studies have shown that a common structure feature of these compounds is their ability to adopt a "butterfly" type shape in this hydrophobic pocket. For successful replication of the viral genome, RT must catalyze a complex series of biochemical reactions in which the single-stranded RNA is converted into a double-stranded DNA copy that will be integrated into the host cell genome [26, 27]. Earlier studies in our lab have focused on providing a complete kinetic and thermodynamic understanding of catalytic activities of HIV-1 RT in the elongation steps involving RNA-dependent and DNA-dependent DNA polymerization as well as RNase H cleavage. Other studies have examined the template switching and strand transfer reactions [28-34]. There is much less kinetic and mechanistic information available concerning the crucial initiation process in which human $tRNA_3^{Lys}$ binds to a region on the RNA genome known as the primer binding site (PBS) and initiates DNA synthesis. Accordingly, during the previous and current periods, one of our objectives has been to examine the reaction kinetics and develop an understanding of the mechanistic details of this tRNA initiation step. These studies were conducted using a model RNA/RNA primer-template, full length synthetic tRNA$_3^{Lys}$, and natural human tRNA$_3^{Lys}$ as a primer. Enzymatic and chemical probing studies have suggested that the formation of the HIV-1 RNA/tRNA$_3^{Lys}$ complex is accompanied by numerous intra- and inter-molecular interactions that result in a highly order structure [35-38]. Interestingly, these interactions require post-transcriptional modifications of tRNA$^{Lys}$ and accordingly, are lacking in studies with synthetic tRNA$_3^{Lys}$ [35, 36, 39, 40].

Role of the Nucleocapsid Protein in HIV RT:

Along with the duplicate copies of the HIV RNA genome, infectious virions contain large amounts of nucleocapsid proteins that are believed to modulate various enzyme activities during the replication of the RNA genome. The two HIV nucleocapsid (NC) proteins receiving the most study are NC p15 and a shortened version NC p7 [41]. These NC proteins contain two zinc finger binding motifs and the structure of NCp7 has been determined [42-44]. The role of NCp7 in HIV-1 viral replication is still not well defined but may be involved in dimerization, packaging of genomic RNA, viral morphogenesis, and the reverse transcription process for RT [45-50]. Thus, in vitro, NCp7 has been shown to (1) promote annealing of the tRNA$_3^{Lys}$ to the PBS [51-53]; (2) accelerate (−) strand DNA transfer during proviral DNA synthesis [32, 51, 54, 55], and (3) enhance processivity and RNase H activity of RT [29, 31, 54, 56, 57]. A direct interaction between NCp7 and RT has been hypothesized and recently demonstrated in vitro [58]. These studies are primarily descriptive in nature and the mechanistic basis of these interactions and the effects of NCp7 on the reaction kinetics of RT have not been examined in detail. Understanding functions of the NC proteins in facilitating replication of the HIV viral genome may provide important insights into potential targets for antiviral chemotherapeutic intervention.

Previous work to develop non-cleavable heterodimers as bifunctional inhibitors has met with limited success and the evidence to date indicates that a true bifunctional two-site inhibitor such as those of the present invention has yet to be realized. To date, all these studies have used cell-based assays to evaluate the efficacy of the bifunctional nucleoside inhibitors, and it is likely that cellular phosphorylation of the bifunctional nucleoside to the triphosphate is a prerequisite for optimal NRTI activity. Therefore, it is unclear whether the lack of activity in earlier reports of bifunctional inhibitors was due to cellular factors such as a failure to be phosphorylated by nucleoside/nucleotide kinases or at the enzyme level due to lack of binding and inhibition of RT.

BRIEF DESCRIPTION OF THE FIGURES

FIG. 9A-C shows the results of experiments using a compound according to the present invention and controls again HIV in MT-2 cells.

BRIEF DESCRIPTION OF THE INVENTION

The present invention to a compound according to the general structure:

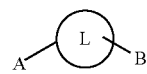

Where A is a nucleoside reverse transcriptase inhibitor (NRTI) compound or a nucleoside competitive reverse transcriptase inhibitor (NCRTI) compound modified to form a chemical bond with said linker group

without significant loss of HIV-1 reverse transcriptase inhibitory activity, B is a non-nucleoside reverse transcriptase inhibitor compound modified to bond to said linker group

without significant loss of HIV-1 reverse transcriptase inhibitory activity and said linker

is a linker group according to the chemical structure:

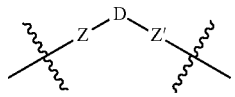

Where Z and Z' are each independently a bond, —(CH$_2$)$_i$—O, —(CH$_2$)$_i$—S, —(CH$_2$)$_i$—N—R,

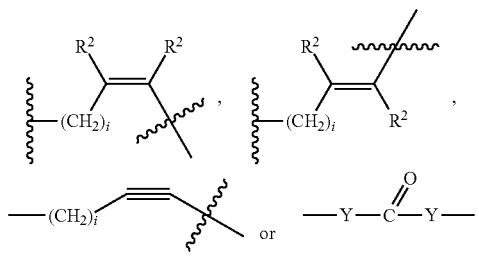

wherein said —(CH$_2$)$_i$ group, if present in Z or Z', is bonded to A or B;
Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 0, 1, 2 or 3;
D is

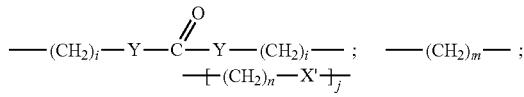

or
a bond, with the proviso that Z, Z' and D are not each simultaneously bonds;
j is 1, 2, 3 or 4,
m is 1, 2, 3, 4, 5 or 6;
n is 1, 2 or 3; and
X' is O, S or N—R
or a pharmaceutically acceptable salt thereof.

In certain aspects of the present invention, the nucleoside reverse transcriptase inhibitor is selected from the group consisting of zidovudine (AZT), lamivudine (3TC), emtricitabine (FTC), abacavir (ABC), stavudine (d4T), didanosine (ddI), dideoxycytidine (ddC), amdoxovir (DAPD), apricitabine (ATC), elvucitabine (B-LFd4C), tenofovir ((9-[9(R)-2-(phosphonomethoxy)propyl]adenine or PMPA) or tenofovir prodrug (tenofovir disoproxil fumarate-9-[(R)-2[[bis[[(isopropoxycarbonyl)oxy]-methoxy]phosphinyl]methoxy]propyl]adenine fumarate), 4'-ethynyl D4T (4'ED4T), 4'-ethynyl-2-fluoro-2'-deoxyadeonsine (4'EFdA), entecavir, Racivir (racemic mixture of ±FTC), In certain aspects of the invention, the non-nucleoside reverse transcriptase inhibitor is selected from the group consisting of nevirapine, delavirdine, efavirenz, TIBO, UC-781 and TMC125.

Figure 1:
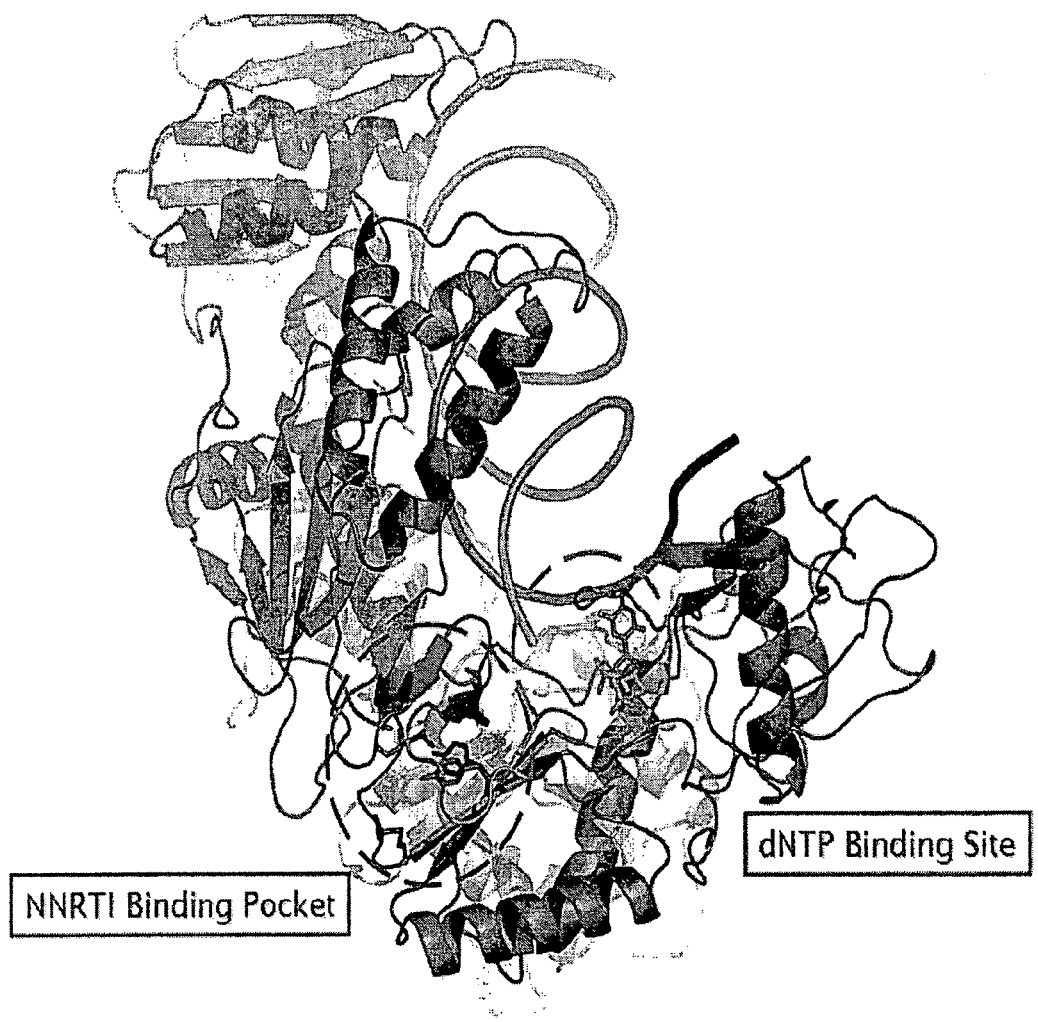
FIG. 1 presents a structure view of HIV-1 RT. The dNTP & NNRTI binding sites are displayed in the figure.
Figure 2:
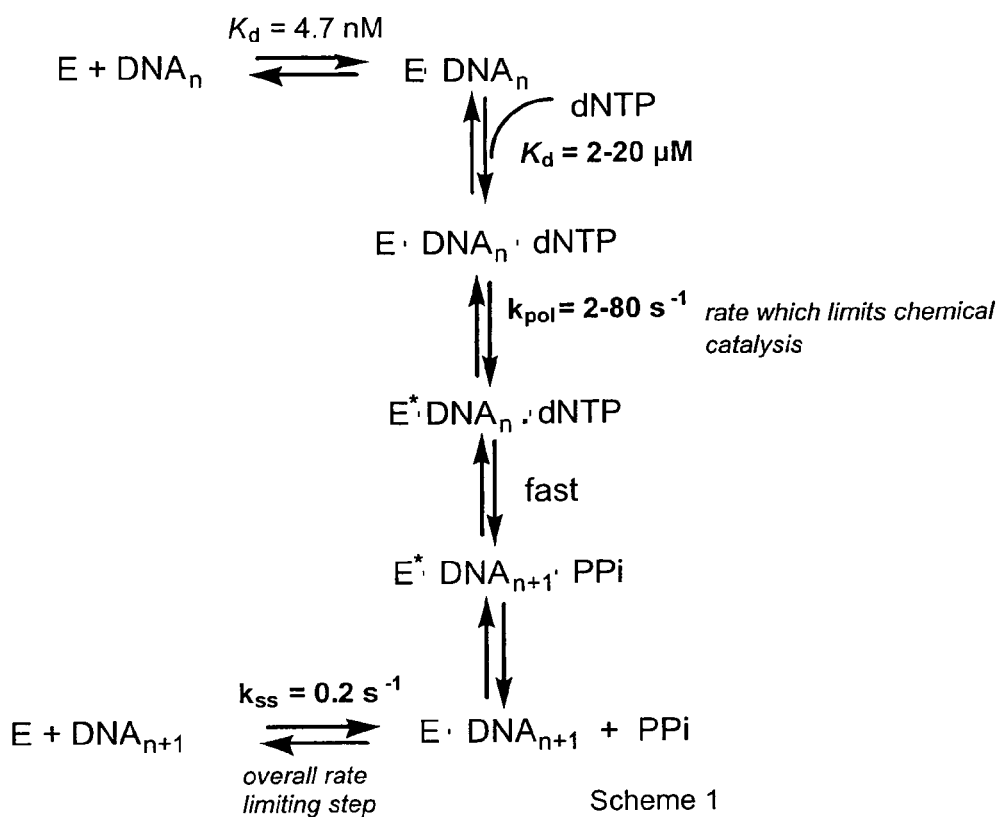
FIG. 2 shows a kinetic model which describes the mechanism of polymerization for HIV RT. This is an ordered mechanism with the DNA binding first followed by the nucleotide.
Figure 3A:
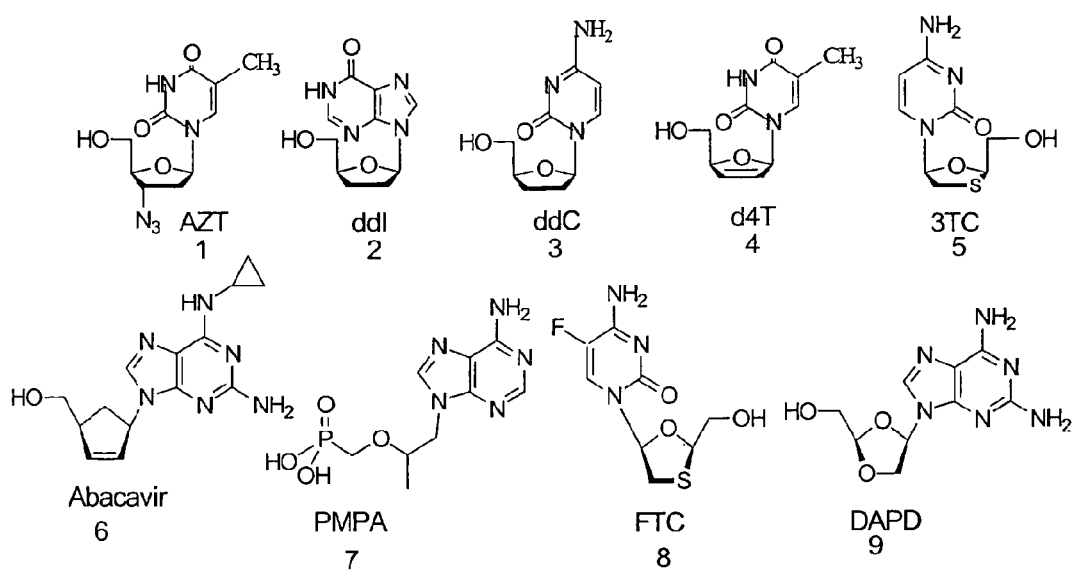
FIG. 3 shows a number of approved nucleoside reverse transcriptase inhibitors (NRTIs).
Figure 3B:
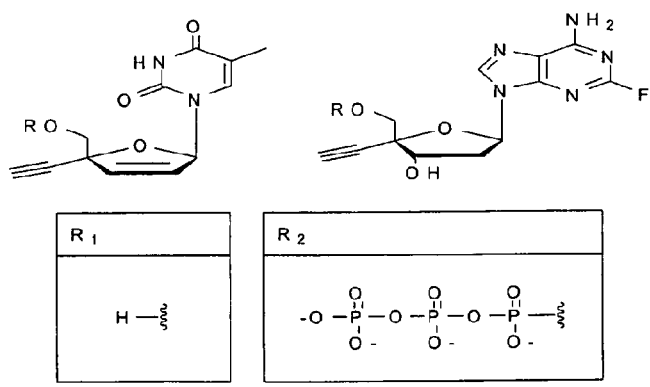
Figure 4:
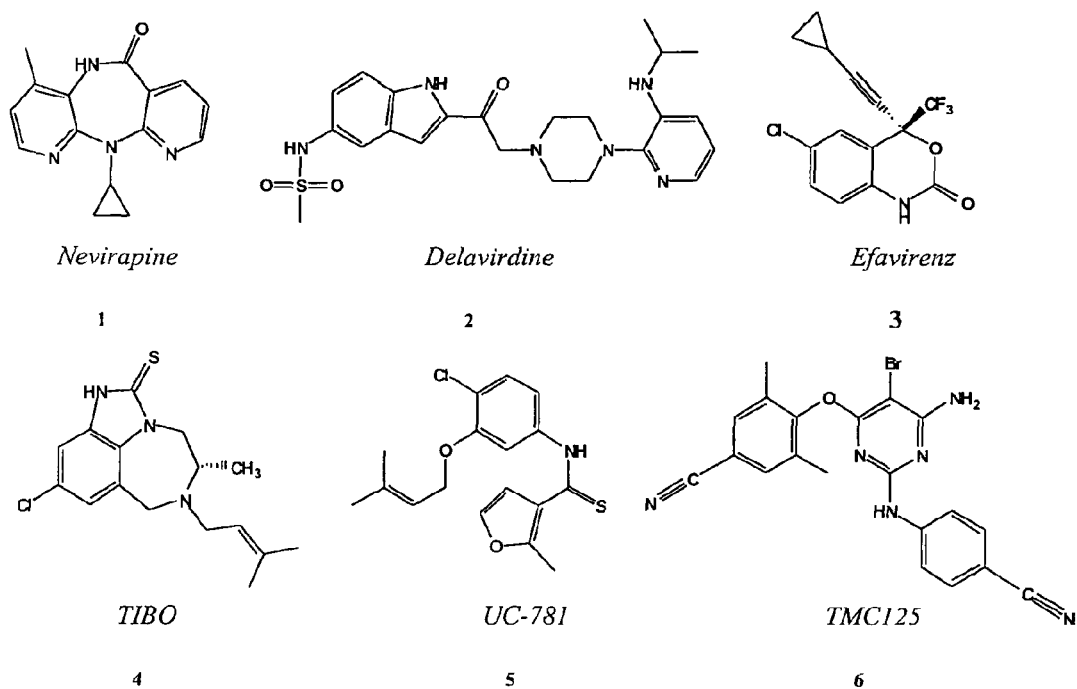
FIG. 4 shows a number of approved and clinically significant non-nucleoside reverse transcriptase inhibitors (NNRTIs).

In certain aspects of the invention, the NRTI is a nucleoside (which may be D or L configured nucleoside) which has a sugar or a related synthon (phosphonomethoxypropyl group, etc.) having a free hydroxyl group (all defined as "sugar synthons"), including, in most instances, a free 5'OH group (see for example, without limitation, FIG. 3). The free 5' OH group may be optionally substituted with an acyl group, a C$_1$-C$_{20}$ alkyl or ether group, an amino acid residue (D or L), a phosphate, diphosphate, triphosphate or phosphodiester group (free acid or salt forms) as otherwise described herein. In instances where the nucleoside base of the NRTI is cytosine, adenine or guanine, the exocyclic amine of the base may be substituted with an acyl group, a C$_1$-C$_{20}$ alkyl group or ether group or an amino acid residue (D or L).

In other aspects of the invention, the NNRTI is selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), 3-Bromo-5-(1-5-bromo-4-methoxy-3-((Adam analog) 5Cl3PhS-2IndolCONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyly)carbonyl]-4-[3-(isopropylamino)-2-pyridinyl]piperazine (piperazine 1pyridine 4 indolyl derivative), 1-[5-[[N-(methyl)methylsulfonylamino]-2-indolylcarbonyl-4-[3-(isopropylamino)-2-pyridinyl]piperazine (piperazine 1pyridine 5 indolyl derivative), 1-[3-(Ethylamino)-2-[pyridinyl]-4-[(5-hydroxy-2-indoly)carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl(pypridin-2(1H)-thione (2-Pyridinone Derivative), 3-[[(2-Methoxy-5, 6-dimethyl-3-pyridyl)methyl]amine]-5-ethyl-6-methyl (pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a] isoindol-5(9bH)-one, Tivirapine (R86183), UC-38, UC-781 and UC-84, among others.

In certain aspects of the invention, the nucleoside reverse transcriptase inhibitor is a cytidine or uridine (thymidine) pyrimidine nucleoside compound which is modified to bond to said linker group at the 5 carbon position of said pyrimidine base of said compound. In certain aspects the nucleoside reverse transcriptase inhibitor is a purine nucleoside compound which is modified to bond to said linker group at a cyclic amine or exocyclic amine position of said purine base or at the 2' or 3' position of the sugar synthon of said compound. In other aspects of the invention, the NRTI is a purine nucleoside compound which is modified to bond to said linker at the C-8 position of the purine base (the carbon position which is generally in the position alpha to the N-position which attaches the base to the sugar synthon).

In certain aspects of the invention, the non-nucleoside reverse transcriptse inhibitor (NNRTI) is bonded to the linker at a position on the NNRTI molecule which is a para or meta position of a phenyl group on the wing-2 (generally, the left hand side of the NNRTI molecule) or otherwise at an atom which is furthermost disposed off of the wing-2 portion of the molecule toward the NRTI active site when the NNRTI molecule is bound to its site in the reverse transcriptase.

Compounds according to the present invention may be used to treat HIV infections in patients and/or to treat patients with ARC or AIDS comprising administering an effective amount of a compound according to the present invention to a patient in need of therapy. In the case of HIV infections, compounds according to the present invention inhibit the growth, elaboration and/or propagation of the virus. In the case of treating patients with ARC or AIDs, administration of effective amounts of compounds according to the present invention to patients in need thereof in order to inhibit the virus and allow the patient's immune system to strengthen or heal and return to a level of normalcy such that a patient's T-cell count will increase and the patient's resistance to disease will increase. In certain preferred aspects of the invention, drug resistant and multiple drug resistant mutants of HIV are effectively treated using one or more bifunctional compound according to the present invention.

In another aspect of the invention, the administration of bifunctional inhibitor compounds according to the present invention reduce the likelihood that a patient with an HIV infection will have the infection worsen into ARC or AIDS. In a further embodiment the administration of bifunctional inhibitor compounds according to the present invention reduce the likelihood that a patient at risk will contract an HIV infection.

In aspects of the invention, compounds according to the present invention are not directed to a compound which comprises d4T as the NRTI, HI-236 as the NNRTI and a butyne group (the acetylenic group being bonded to the 5 position of d4T) as the linker group. In aspects of the invention, compounds according to the present invention are not directed to a compound which comprises AZT as the NRTI, TSAO-T as the NNRTI and an alkylene $((CH_2)_n)$ linker which binds amine groups (N-3) in the thymine rings of AZT and TSAO-T. In aspects of the invention, compounds according to the present invention are not directed to a compound which comprises d4T as the NRTI, benzoylhexamethylene [imidazo{1,5-b}pyridazine] as the NNRTI and an alkylene diamine (e.g., 1N-methyl,1,2 ethyldiamine) as the linker.

Figure 5:
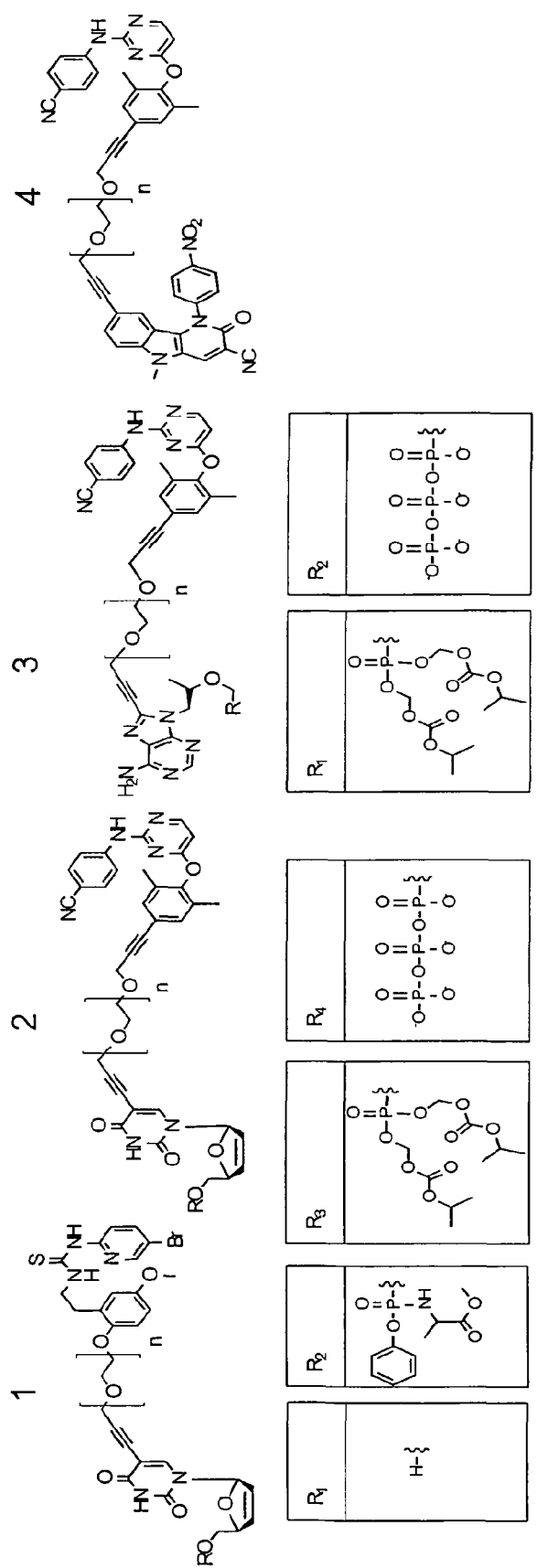
FIG. 5 shows the nucleoside reverse transcriptase inhibitors 4'-ethynyl D4T (4'ED4T), 4'-ethynyl-2-fluoro-2'-deoxyadeonsine (4'EFdA) and their corresponding phosphorylated (triphosphate) analogs.

In certain aspects of the invention, the bifunctional compound according to the present invention is a compound as set forth in attached FIG. 5 hereof. Note that compounds according to the present invention include those which contain phosphoramidate ($R_2$), phosphodiester ($R_3$-dioxycarbonyl esters) or triphosphate (as free acid or salt) groups.

DETAILED DESCRIPTION OF THE INVENTION

The following terms shall be used throughout the specification to describe the present invention. Unless otherwise indicated, a term used to describe the present invention shall be given its ordinary meaning as understood by those skilled in the art.

The term "compound", as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds such as NRTI's, NCRTI's or NNRTI's which have been modified to facilitate the administration and delivery of compounds to a site of activity.

The term "patient" or "subject" is used throughout the specification within context to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective" is used herein, unless otherwise indicated, to describe an amount of a compound or composition which, in context, is used to produce or effect an intended result, whether that result relates to the treatment of a viral, microbial or other disease state, disorder or condition associated with HIV, ARC or AIDS or alternatively, is used to produce another compound, agent or composition. This term subsumes all other effective amount or effective concentration terms which are otherwise described in the present application.

The term "inhibitory effective concentration" or "inhibitory effective amount" is used throughout the specification to describe concentrations or amounts of compounds according to the present invention which substantially or significantly inhibit the growth or replication of the HIV virus. This term, used in context, is subsumed under the generic term "effective", defined above.

The term "preventing effective amount" is used throughout the specification to describe concentrations or amounts of compounds according to the present invention which reduce the likelihood of infection or delaying the onset of infections and related conditions. This term, used in context, also is subsumed under the generic term "effective", defined above.

The term "sugar synthon" shall mean, within a nucleoside reverse transcriptase inhibitor, a ribose or other sugar-like moiety (dioxolane, thioxolane, carbocyclic groups, etc.), including, for example, a simple alkyl ether, including an alkyl ether phosphonate of PMPA, which extends from the purine or pyrimidine base and may be used to chemically bond a nucleoside reverse transcriptase inhibitor to a non-nucleoside reverse transcriptase inhibitor through a linker group.

The term "heteroaryl" shall mean a 5-12-membered heteroaromatic ring or fused ring system containing 1 to 5 heteroatoms selected from oxygen, nitrogen and sulfur, which heteroaromatic ring(s) is/are each optionally substituted with from 1 to 3 substituents such as halogen, hydroxyl, $C_{1-3}$ alkyl, $C_{1-3}$ alkoxy and $CF_3$. The terms heteroaryl and "heteroaromatic ring" are used interchangeably herein. Exemplary heteroaryl groups include, for example, pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole, phenothiazine, pyrrolopyrimidine, pyrrolopyrazine and furopyrimidine, among numerous others The term "human immunodeficiency virus" or "HIV" shall be used to describe human immunodeficiency viruses 1 (HIV-1).

The term "drug resistant" or "multiple drug resistant" refers to strains of the HIV virus which have mutated to be resistant to one or more clinically approved anti-HIV agents, in particular, HIV strains which are resistant to one or more NRTI, NCRTI and/or NNRTI compounds. The compounds may be resistant to one or more of the clinically important NRTI, NCRTI and/or NNRTI, but usually, drug resistant and multiple drug resistant strains include primarily those HIV strains which are resistant to nucleoside reverse transcriptase inhibitors. Exemplary HIV drug resistant strains which may be effectively treated using compounds according to the present invention include the following, among others:

Exemplary drug resistant strains (defined by RT mutation) of HIV are selected from the group consisting of XXBRU, K65R, Y115F, F116Y, Q151M, M184V, L74V, V75T, 4XZT, T215Y, K103N, T215Y/M184V, 5705-72, 488-101, C910-6, LA1M184V, G910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H among others.

A complex pattern of viral resistance has emerged with long-term nucleoside therapy. In general, cross-resistance with various nucleoside analogs is not common, although there are exceptions. There are three regions of the reverse transcriptase protein that are important in developing nucleoside resistance.[91] First a loop strand of β sheet containing residues 62-77 appears to be a "hot spot" for amino acid substitutions such as L74V, V75T. This "templating base" region is located in the fingers domain which contacts the template strand of the substrate. The second region is "active site" in the palm domain in an area of the HIV RT polymerase that is highly conserved among polymerases, containing the YMDD motif. For HIV-RT, key resistance mutations include: K65R, Y115F, F116Y, Q151M and M184V [92-99]. The third region contains the putative "ATP binding site" and includes: M41L, D67N, K70R, T215Y/F and K219Q/E that are also located in the palm domain and are close to the hydrophobic binding pocket in which the non-nucleoside inhibitors such as nevirapine bind [100-102]. The rapid emergence of resistance to the non-nucleoside analogs is the major limitation to their clinical usefulness. This is primarily due to mutations in HIV-1 RT (Y181C, K103N, L100I, Y188C/H) that define the hydrophobic binding pocket for non-nucleoside analogs [25]. Another mutation, P236L, associated with delavirdine resistance is suggested to be impair RNAse H activity [103]. These mutations may arise so readily because they do not significantly affect RT function as they are in a site proximal to the catalytic site. Recent reports also suggest that the RNAse H and connection domains may also play a role in NRTI, NCRTI and NNRTI resistance [104-107].

The term "reverse transcriptase" shall mean the reverse transcriptase enzyme of HIV-1.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), below, then the patient falls within this category. If the patient's t-cell count has ever dropped below 500, that patient is considered either Category 2 (ARC) or Category 3 (AIDS).

A Category 2 (ARC) infection is characterized by the following criteria: The patient's T-cells have dropped below 500 but never below 200, and that patient has never had any Category 3 diseases (as set forth below) but have had at least one of the following illnesses Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ
Constitutional symptoms (fever≧38.5° C.) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess and/or
Peripheral neuropathy According to the U.S. government, Category 2 ARC infections are defined by an immune system showing some signs of non-life threatening damage.

A Category 3 (AIDS) infection is characterized by the following criteria: the patient's T-cells have dropped below 200 or the patient has had at least one of the following defining illnesses Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)
Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
Pneumocystis carinii pneumonia Pneumonia, recurrent
Progressive multifocal leukoencephalopathy
*Salmonella septicemia*, recurrent
Toxoplasmosis of brain
Wasting syndrome due to HIV The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Compounds according to the present invention may be administered with one or more additional anti-viral agent, including anti-HIV agents such as stand alone (i.e., non-chimeric bifunctional) nucleoside reverse transcriptase inhibitors (NRTI), nucleoside competitive reverse transcriptase inhibitor (NCRIT), non-nucloeoside reverse transcriptase inhibitors (NNRTI), protease inhibitors, fusion inhibitors and intetgrase inhibitors, among others The term "nucleoside reverse transcriptase inhibitor" or "NRTI" is used to describe a compound which is a nucleoside analog and inhibits reverse transcriptase of HIV-1. NRTI compounds for use in the present invention include for example, zidovudine (AZT), lamivudine (3TC), emtricitabine (FTC), abacavir (ABC), stavudine (d4T), didanosine (ddI), dideoxycytidine (ddC), amdoxovir (DAPD), apricitabine (ATC), elvucitabine (B-LFd4C), tenofovir ((9-[9(R)-2-(phosphonomethoxy)propyl]adenine or PMPA) or tenofovir prodrug (tenofovir disoproxil fumarate-9-[(R)-2[[bis[[(isopropoxycarbonyeoxy]-methoxy]phosphinyl]methoxy]propyl]adenine fumarate), 4'-ethynyl D4T (4'ED4T), 4'-ethynyl-2-fluoro-2'-deoxyadeonsine (4'EFdA), entecavir (a guanosine nucleoside analog), Racivir (racemic mixture of ±FTC), among others. It is noted that in the present invention in providing for bifunctional chimeric compounds which comprise a NRTI or NcRTI, a linker and a NNRTI, pyrimidine nucleoside compounds (those which have a uracil, thymine or cytosine base in the nucleoside) are generally attached to the chemical linker (which links the NRTI to the NNRTI) at the 5 position of the base (i.e., at the unsaturated carbon position furthest from the nitrogen to which the base is attached to the sugar synthon) or alternatively at the 4' position of the sugar synthon (such as the 4'ethynyl position of 4'ED4T).

The term "nucleoside competitive reverse transcriptase inhibitor" or "NCRTI" is used to describe a compound which is not a nucleoside analog, but which competes with NRTI for inhibition of HIV-1 reverse transcriptase. Examples of these compounds include the intopy compounds which are disclosed in international application publication WO2004/046143, published 3 Jun. 2004, which designates the United States, which is incorporated by reference herein. Although any number of compounds which are disclosed in WO2004/046143 may be used in the present invention, NcRTI compounds which find particular use in the present invention include compounds according to the general structure:

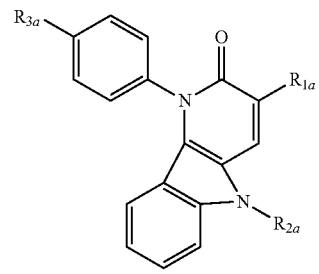

Where $R_{3a}$ is cyano (CN) or Nitro ($NO_2$);
$R_{1a}$ is cyano, nitro, methyloxycarbonyl, methylaminocarbonyl, ethyloxycarbonyl or ethylaminocarbonyl; and
$R_{2a}$ is H or a $C_1$-$C_4$ alkyl group which may be optionally substituted with a hydroxyl group.

A preferred NcRTI compound which is optionally used in the present invention has the chemical structure:

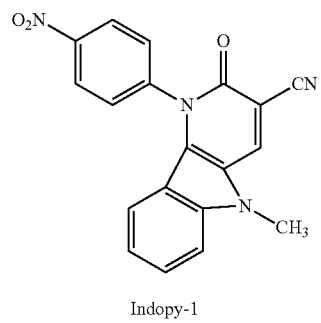 [SMILES: Cn1c2ccccc2c2c1cc(C#N)c(=O)n2-c1ccc([N+](=O)[O-])cc1]

Indopy-1

Attachment to a linker in the present invention is preferably on the position of the molecule in the benzene ring of the indole moiety of the indopy compounds preferably at a position on the benzene ring furthest from nitrogen in the indole moiety or alternatively, at the nitrogen of the indole moiety may afford bifunctional anti-HIV agents according to the present invention.

Another compound (NNRTI) which is optionally used in the present invention to create bifunctional compounds is

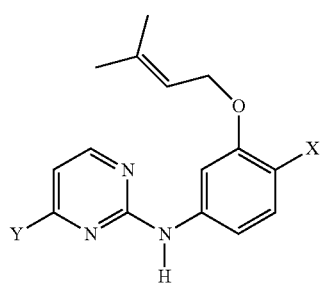

JL00135

Where X is a halogen (F, Cl, Br or I) or a cyano group and Y is OH or OMe.

Another compound(s) which is optionally used in the present invention has the chemical structure:

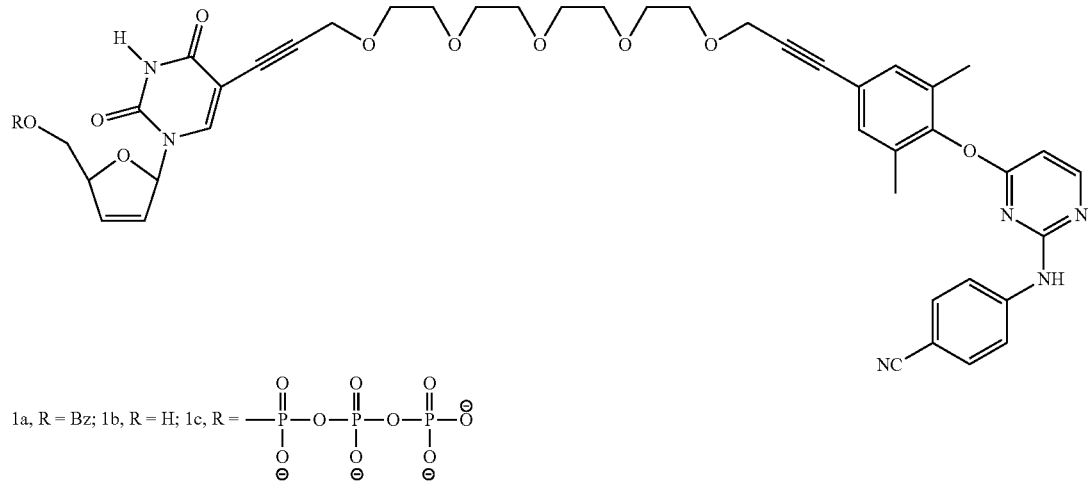

1a, R = Bz; 1b, R = H; 1c, R = triphosphate

Where R is H, an acyl group, alkyl group, ether group, amino acid group, mono-di- or triphosphate or phosphodiester group as otherwise described herein.

Figure 6:
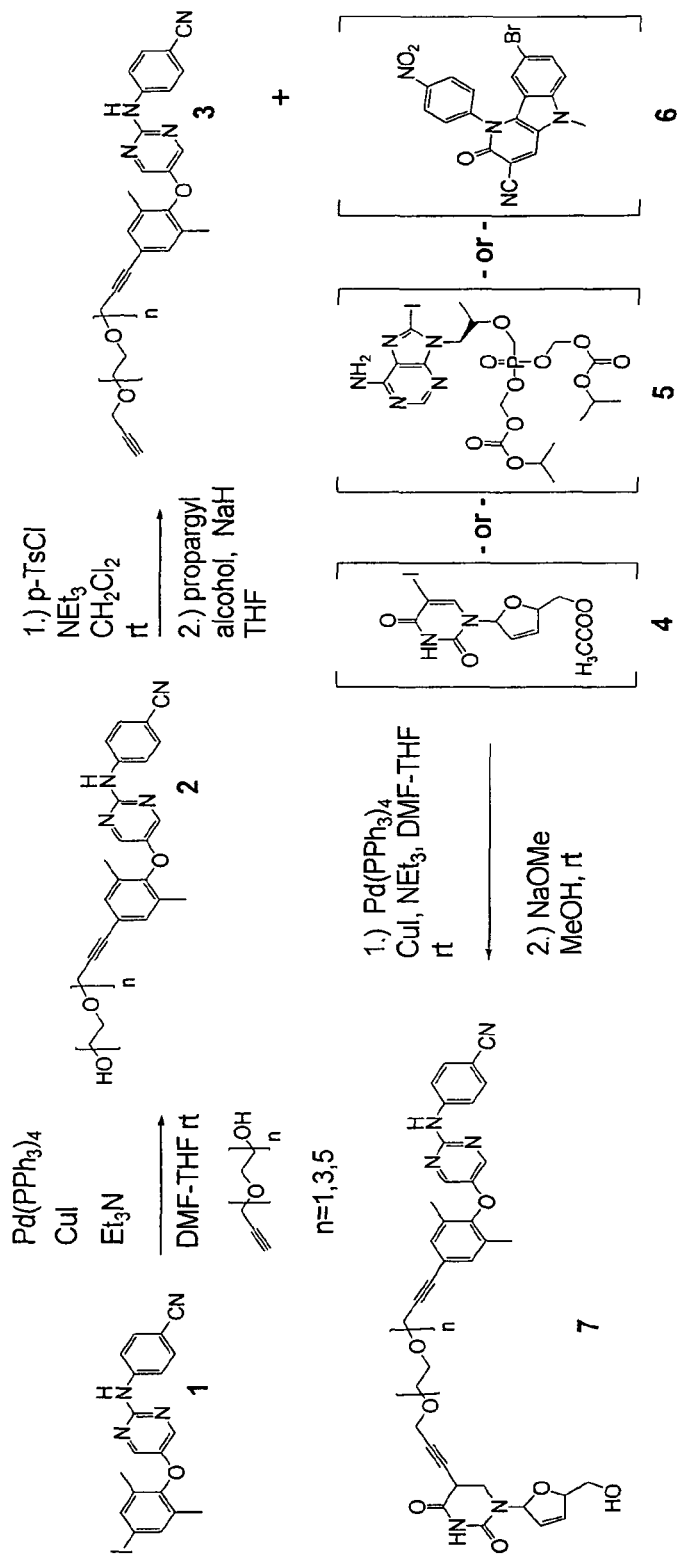
FIG. 6 shows the nucleoside reverse transcriptase inhibitors Dioxolane guanosine (DXG), Carbovir (CBV), Dideoxydidehydro guanosine (D4G) and cyclopropylamine prodrug of D4G (Cyclo-D4G) and their corresponding phosphorylated (triphosphate) analogs.

Other compounds useful in the present invention are those which are found in FIGS. 5 and 6, attached hereto.

The term "non-nucleoside reverse transcriptase inhibitor" or "NNRTI" is used to describe a compound which also inhibits reverse transcriptase, but does so in a manner which is non-competitive to the NRTI and binds to a site (allosteric) in the reverse transcriptase which is different from the binding site of the NRTI or NcRTI but which facilitates inhibition of reverse transcriptase. Exemplary NNRTI compounds for use in the present invention include nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl]hept-1-enyl)-2-methoxybenzoate (Alkenyldiarylmethane analog, Adam analog), 5Cl3PhS-2IndolCONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyly)carbonyl]-4-[3-(isopropylamino)-2-pyridinyl]piperazine (piperazine 1pyridine 4 indolyl derivative), 1-[5-[[N-(methyl)methylsulfonylamino]-2-indolylcarbonyl-4-[3-(isopropylamino)-2-pyridinyl] piperazine (piperazine 1pyridine 5 indolyl derivative), 1-[3-(Ethylamino)-2-[pyridinyl]-4-[(5-hydroxy-2-indolyl) carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethy]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl(pypridin-2(1H)-thione (2-Pyridinone Derivative), 3-[[(2-Methoxy-5, 6-dimethyl-3-pyridyl)methyl]amine]-5-ethyl-6-methyl (pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a] isoindol-5(9bH)-one, Tivirapine (R86183), UC-38, UC-781 and UC-84, among others. The NNRTI is substituted on a position of the molecule where binding to and inhibition of reverse transcriptase is least affected by linkage to the NRTI. See the website: niaid.nih.gov/daids/dtpdb/nnrti1.htm Attachment of the NNRTI to the linker is preferably at a site on the wing-2 position of the NNRTI (generally the left portion of the NNRTI molecule) furthermost away from the center of the NNRTI molecule (e.g., in the case of a phenyl group, at a para or meta position of the phenyl group). In functional terms, this attachment site in the NNRTI molecule affords the linker an accommodative steric position to link the NNRTI molecule bound to the NRTI molecule and have the NNRTI molecule most effectively bound to its site in the reverse transcriptase and the NRTI to be most effectively bound to its site in the reverse transcriptase.

The term "HIV integrase inhibitor" is used to describe a class of antiretroviral drugs designed to block the action of integrase, a viral enzyme that inserts the viral genome into the DNA of the host cell. Since integration is a vital step in retroviral replication, blocking it can halt further spread of the virus. Integrase inhibitors were initially developed for the treatment of HIV infection, but they could be applied to other retroviruses. The first integrase inhibitor approved for use by the US Food and Drug Administration (FDA) was Raltegravir (Isentress). Since integrase inhibitors target a distinct step in the retroviral life cycle, they may be taken in combination with other types of HIV drugs to minimize adaptation by the virus. They are also useful in salvage therapy for patients whose virus has mutated and acquired resistance to other drugs. Exemplary HIV integrase inhibitors include Raltegravir and Elvitegravir, among others.

The term "HIV protease inhibitor" is used to describe a class of anti-HIV drugs designed to inhibit the enzyme protease and interfere with virus replication. Protease inhibitors prevent proteases from splitting proteins into peptides and prevent the cleavage of HIV precursor proteins into active proteins, a process that normally occurs when HIV replicates. Exemplary protease inhibitors include saquinavir (Invirase, Fortovase) and ritonavir (Norvir). Often they are administered as part of a two- or three-drug cocktail, accompanied by one or more nucleoside antiviral drugs. They are used in combination with the chimeric anti-HIV compounds according to the present invention.

The term "HIV fusion inhibitor" is used to describe a class of antiretroviral drugs, used in combination therapy for the treatment of HIV infection. This class of drugs interferes with the binding, fusion and entry of an HIV virion to a human cell. By blocking this step in HIV's replication cycle, such agents slow the progression from HIV infection to AIDS. Exemplary agents include Maraviroc, Enfuvirtide, Vicriviroc, Aplaviroc, TNS-355, PRO140 and BMS-488043, among others.

The terms "linker" and "tether" are used synonymously to describe a chemical chemical entity connecting a nucleoside reverse transcriptase inhibitor (NRTI) and a non-nucleoside reverse transcriptase inhibitor (NNRTI) through covalent bonds. The linker between the two active compounds is about 5 Å to about 20 Å or more in length, about 6 Å to about 19 Å in length, about 7 Å to about 18 Å in length, about 8 Å to about 17 Å in length, about 9 Å to about 16 Å in length, about 10 Å to about 15 Å in length, about 7 Å to about 15 Å in length, about 5 Å to about 16 Å in length, about 10 Å to about 20 Å in length. By having a linker with a length as otherwise disclosed herein, the NRTI and the NNRTI may simultaneously interact with reverse transcriptase of HIV-1, providing optimal activity and in many cases, synergistic inhibitory activity of reverse transcriptase. The selection of a linker component is based on its documented properties of biocompatibility, solubility in aqueous and organic media, and low immunogenicity/antigenicity. A linker based upon polyethyleneglycol (PEG) linkages is favored as a linker because of its chemical and biological characteristics.

The term "pharmaceutically acceptable salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of HIV infections, ARC or AIDS, the term "salt" shall mean a pharmaceutically acceptable salt, consistent with the use of the compounds as pharmaceutical agents.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical. The term "ether" shall mean a $C_1$ to $C_{20}$ ether group, formed from an oxygen and an alkyl group at a position on the sugar moiety of compounds according to the present invention, or alternatively, may also contain at least one oxygen group within the alkyl chain.

The term "acyl" is used in the specification to describe a group at the 5' position of the nucleoside analog (i.e., at the free hydroxyl position in the sugar synthon) which contains a $C_1$ to $C_{20}$ linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention are represented by the structure:

where $R_4$ is a $C_1$ to $C_{20}$ linear, branched or cyclic alkyl group, alkoxyalkyl, aryloxyalkyl, such as phenoxymethyl, aryl, alkoxy, alkoxycarbonyl, alkoxycarbonyloxy (e.g., [(isopropoxycarbonyl)oxy]-methoxy), among others. Preferred acyl groups are those where $R_4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others including mesylate groups. One of ordinary skill in the art will recognize the acyl groups which will have utility in the present invention, either to synthesize the target pharmaceutical compounds or as prodrug forms of the nucleosides according to the present invention.

The term "phosphate ester" or "phosphodiester" is used throughout the specification to describe mono-phosphate groups (as the free acid or various salt forms) at the 5' position of the dioxanyl moiety or sugar synthon which are diesterified such that the phosphate group is rendered neutral, i.e., has a neutral charge. Phosphate esters for use in the present invention include those represented by the structures:

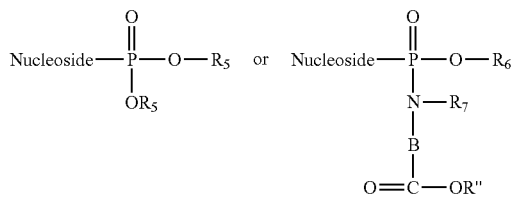

where $R_5$, $R_6$ and $R''$ are selected from a $C_1$ to $C_{20}$ linear, branched or cyclic alkyl group, alkoxyalkyl, aryloxyalkyl, such as phenoxymethyl, aryl and alkoxy, alkoxycarbonyl, alkoxycarbonyloxy (e.g., [(isopropoxycarbonyl)oxy]-methoxy), among others, B is a direct bond (attaching the nitrogen to the ester/carboxylic group) or a $C_1$-$C_3$ alkylene group optionally substituted with a $C_1$-$C_3$ alkyl group, preferably a methyl group, and $R_7$ is H, a $C_1$ to $C_{20}$ linear, branched or cyclic alkyl or acyl group, alkoxyalkyl, aryloxyalkyl, such as phenoxymethyl, aryl and alkoxy, among others. Preferred monophosphate esters for use in prodrug forms according to the present invention are those where $R_5$ is a $C_1$ to $C_{20}$ is a linear or branched chain alkyl group or a phenyl group (optionally substituted with 1 or more methoxy or methyl groups), more preferably a $C_1$ to $C_3$ alkyl group or a phenyl group.

The term "amino acid" or "amino acid residue" shall mean, within context, a radical of a D- or L-amino acid which is covalently bound to a nucleoside analog at the 4' exocyclic amine position of the cytosine base or a hydroxyl position (e.g., the 5', 3', 2'-OH position) of the sugar synthon through a carboxylic acid moiety of the amino acid, thus forming respectively, an amide or ester group linking the NRTI to the amino acid. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others.

The term "protecting group" or "blocking group" shall mean, within its context (generally, the chemical synthesis of compounds according to the present invention), a chemical group or moiety which is used to prevent an otherwise active moiety such as an amine, hydroxyl or mercapto group from reacting in a given reaction scheme and which is readily removed under mild conditions which do not otherwise undesirably affect the molecule or compound to which the protecting group is bonded. In the present invention, numerous protecting groups may be used to produce compounds according to the present invention, preferred groups include the benzoate group to protect or block a primary or secondary hydroxyl group, oxycarbonyl groups and related groups to protect hydroxyl and amine functional groups, triphenylmethyl and substituted phenyl methyl groups to protect hydroxyl and amine groups and silyl groups (in particular, a tertiary butyl dimethyl silyl, a tertiary butyl diphenyl silyl group or a trimethylsilyl group or a related silyl protecting group) to block primary (or secondary) hydroxyl groups. One of ordinary skill in the art will recognize the various protecting groups which may be utilized within context in producing compounds and intermediates according to the present invention.

amounts of the individual compounds will be present in the patient at the same time.

Compounds according to the present invention may be used in pharmaceutical compositions having biological/pharmacological activity for the treatment of, for example, viral infections, as well as a number of other conditions and/or disease states which may appear or occur secondary to the viral infection. These compositions comprise an effective amount of any one or more of the compounds disclosed hereinabove, optionally in combination with a pharmaceutically acceptable additive, carrier or excipient. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph, Hely, or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of novel nucleoside of the instant invention that may be combined with the carrier materials to produce a single dosage form will vary depending upon the host treated, the particular mode of administration. Preferably, the compositions should be formulated so that a dosage of between about 0.01 and 150, preferably about 0.5 to about 25 mg/kg of patient/day of the novel nucleoside can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral-preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay the onset of viral infections of humans and in particular HIV infections. In its preferred embodiments, the compounds are used to treat HIV and related conditions such as ARC and AIDS. Preferably, to treat, prevent or delay the onset of a viral infection, the compositions will be administered in oral dosage form in amounts ranging from about 250 micrograms up to about 500 mg or more at least once a day, preferably, up to four times a day, within the dosage range used for therapeutic treatment. The present compounds are preferably administered orally, but may be administered parenterally, topically, in suppository or other form.

The compounds according to the present invention, because of their low toxicity to host cells, may advantageously be employed prophylactically to prevent a viral infection or to prevent the occurrence of clinical symptoms associated with the viral infection, for example ARC or AIDS secondary to HIV. Thus, the present invention also encompasses methods for the prophylatic treatment (preventing, reducing the likelihood or delaying the onset) of HIV infections and conditions which occur secondary to HIV infections. This prophylactic method comprises administering to a patient in need of such treatment or who is at risk for the development of an HIV infection, an amount of a compound according to the present invention effective for alleviating, preventing or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (as described hereinabove, as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other anti-viral agents for the treatment of a virus infection as otherwise described herein, especially including other compounds of the present invention or compounds which are otherwise disclosed as being useful for the treatment of HIV or other virus infections which occur secondary to HIV infections, including those stand alone agents presently used to treat HIV such as nucleoside reverse transcriptase inhibitors (NRTI), non-nucleoeoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development, among others as well as compounds which are disclosed in inter alia, U.S. Pat. Nos. 6,240,690; 6,316, 505; 6,316,492; 6,232,120; 6,180,604; 6,114,327; 5,891,874; 5,821,242; 5,532,215; 5,491,135; 5,179,084; and 4,880,784, among others, relevant portions of which are incorporated by reference herein.

The compounds disclosed in the above-referenced patents may be used in combination with the present compounds for their additive activity or treatment profile against HIV and/or other viruses and in certain instances, for their synergistic effects in combination with compounds of the present invention. The bifunctional compounds according to the present invention in many cases provide synergistic activity (i.e., more than additive) compared to compounds administered as stand alone compounds. Secondary or additional compounds for use with the present compounds are those which do not inhibit HIV or another virus. Certain compounds according to the present invention may be effective for enhancing the biological activity of certain agents according to the present invention by reducing the metabolism or inactivation of other compounds and as such, are co-administered for this intended effect.

It is noted that compounds according to the present invention promote synergistic anti-HIV activity through the dual antagonist action of the compound. By binding to HIV-1 reverse transcriptase at both binding sites of NRTI/NcRTI (active binding site) and NNRTI (allosteric binding site) simultaneously, a synergistic inhibitory effect is realized. The activity of the present compounds are particularly useful for treating mutant/drug resistant strains of HIV and through their dual antagonist activity, the present compounds reduce the likelihood that a population of virus will mutate and give rise to a drug resistant (DR) or multiple drug resistant (MDR) populations of HIV virus.

The present invention is now described, purely by way of illustration, in the following examples. It will be understood by one of ordinary skill in the art that these examples are in no way limiting and that variations of detail can be made without departing from the spirit and scope of the present invention.

Chemistry

In general, to produce compounds according to the present invention, chemical synthesis proceeds in each instance within context by first linking a nucleoside reverse transcriptase inhibitor (NRTI), nucleoside competing reverse transcriptase (NcRTI) or non-nucleoside reverse transcriptase inhibitor (NNRTI) to a linker as otherwise described herein to form a NRTI-linker intermediate, a NcRTI-linker intermediate, or a NNRTI-linker intermediate, which is then further reacted as appropriate with a NRTI, NcRTI or NNRTI to provide the present compounds. The synthetic chemical methods employed are well-known in the art, including the use of appropriate protecting groups, leaving groups, nucleophilic groups and electrophilic groups to facilitate covalent binding of the linker group to respectively, the NRTI or NcRTI and the NNRTI.

It is noted that in order to maintain the integrity and binding of the individual components of compounds according to the present invention, the linker site on the NRTI, NcRTI and the NNRTI (i.e., the atom to which the linker is bonded) is chosen to avoid or minimize disruption to the binding of the component with its binding site in reverse transcriptase. Thus, in the case of NRTI which contain pyrimidine (uracil, thymine, cytosine) bases, attachment of the linker is made preferably at the 5-position (at the double bond, at the carbon furthest away from attachment of the ring nitrogen atom to the sugar synthon. Other attachment positions may also be useful, including attachment at the 6-position of the base, depending upon the linker used. In the case of purine based NRTI, attachment of the linker is preferably at the C-8 position of the base (i.e., the carbon position in the 5-membered ring nearest the attachment of the sugar synthon at N-9). Attachment of the linker at these positions in the pyrimidine and purine base, respectively, reduces the impact that such linking has on base pairing of the NRTI in the active site of reverse transcriptase, an important consideration in maintaining and/or enhancing inhibition.

In the case of NcRTI compounds, attachment of the linker is preferably made in the benzene ring of the indole chemical moiety (portion of the fused three-ring) preferably at the carbon position in that benzene ring furthest from the nitrogen.

By way of example, compounds according to the present invention as depicted below

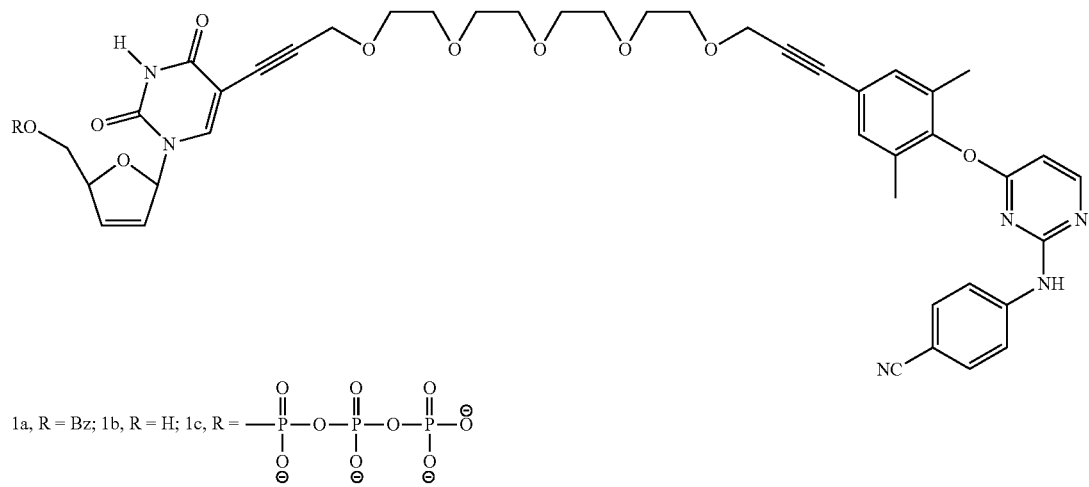

1a, R = Bz; 1b, R = H; 1c, R = —P(=O)(O⁻)—O—P(=O)(O⁻)—O—P(=O)(O⁻)—O⁻ were synthesized according to the following scheme I:

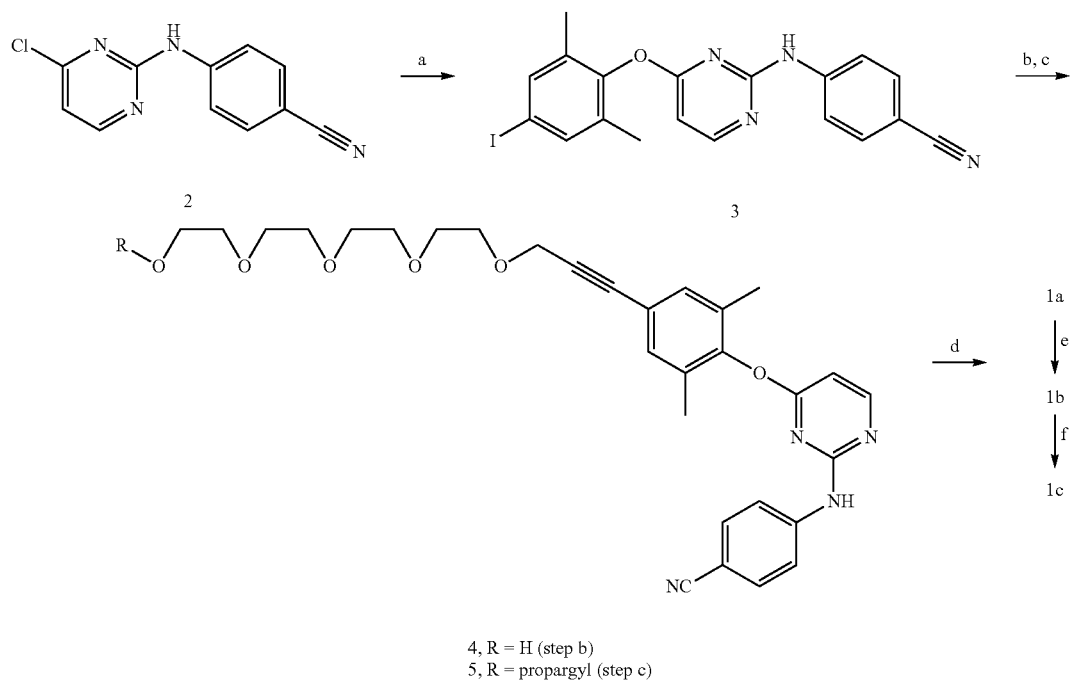

4, R = H (step b)
5, R = propargyl (step c)

As per scheme I above, the synthesis of 1a began with targeting quantities of the known pyrimidine derivative 2 (Scheme 1), (Ludovici, et al., *Bioorg. Med. Chem. Lett.*, 2001 11, 2235) which underwent nucleophilic substitution in high yield to 3 with 4-iodo-2,6-dimethylphenol using cesium carbonate as base. Subsequent Sonogashira coupling with the monopropargyl ether of 4-PEG-diol (Veciana, et al, *Synthesis,* 1992, 1164) to give tethered TMC-derivative 4, followed by hydroxyl group propargylation gave 5, which was subjected to a further Sonogashira coupling with 5'-benzoyl-5-iodo-d4U (Hunter, et al., *Bioorg. Med. Chem. Lett.,* 2007, 17, 2614) to afford bifunctional benzoate 1a in around 60% isolated yield. Deprotection of 1a with sodium methoxide (1 equiv), quenching with acetic acid (1 equiv) and direct silica-gel flash chromatography without a work-up afforded target nucleoside 1b in 94% yield. Transformation to its triphosphate 1c proved to be problematic in that direct phosphorylation using Yoshikawa's procedure (Burgess and Cook, *Chem. Rev.,* 2000, 100, 2047) with $POCl_3$ and trimethyl phosphate failed to give the desired product. Convergent cross-coupling of the 5'-triphosphate of 5-iodo-d4U as a tetra(triethylammonium) salt with alkyne 5 using a homogeneous (Thoresen, et al., *Chemistry-A European Journal,* 2003, 9, 4603) Sonogashira reaction in DMF appeared to produce the product by TLC, but separation from the copper reagent proved to be problematic. Finally, nucleoside 1b was successfully converted in 37% isolated yield into triphosphate 1c using Eckstein's procedure. (Eckstein and Ludwig, *J. Org. Chem.*, 1989, 54, 631). The product was purified using Sephadex (DEAE) ion-exchange chromatography with aq. triethylammonium bicarbonate (1M)/$H_2O$ as the mobile phase to afford 1c as a film. $^1H$ and $^{13}C$ NMR spectroscopy identified 1c to exist as a tris(triethylammonium) salt, with the other cation provided by an internal pyrimidinium ion. The triphosphate also revealed the necessary doublet, doublet, triplet array in its $^{31}P$ NMR spectrum, as well as a single peak in its HPLC, and correct molecular ion (M−H$^+$, 1031.2035) in its HRMS ESI/MS (see supporting info). The parent TMC derivative, a TMC derivative with a 4-PEG unit linker were also synthesized, and together with the triphosphate of the bifunctional nucleoside: d4U-TP-4PEG-TMC (1c) and the bifunctional nucleoside (1b) were all assessed for their interaction with HIV-1 RT.

Synthesis of the bifunctional compounds which are presented in FIG. 5 proceed via the scheme which is presented in FIG. 6. As illustrated in the convergent Scheme 2, presented in FIG. 6, an iodo version of the TMC analog was synthesized in which the nitrile is replaced with an iodine. This allows for PEG linker attachment via a Sonagashira coupling and further elaboration by coupling to the NRTI. This synthetic route is adaptable to accommodate a number of linker lengths and types, NNRTIs, and NRTIs. As shown in Scheme 3 the iodo-d4U, 4, can be coupled with 3, which is then deprotected to yield the nucleoside bifunctional, 7. This strategy is easily adaptable to use 5 or 6 for changing the NRTI moiety and coupling with the functionalized NNRTI such as the TMC-linker illustrated by 3 (FIG. 6).

Other compounds may be synthesized using analogous and standard chemical synthetic methods available in the art to provide linked NRTI (NcRTI)-NNRTI compounds according to the present invention.

Biological Activity

The compounds 1b, 1c, above are first evaluated for their ability to inhibit HIV-RT at a biochemical level using a steady-state competition assay to determine potency to inhibit dTTP incorporation opposite A into a radiolabeled D23/D36mer primer-template (Table S1, below). The $IC_{50}$ values were determined for in vitro inhibition of RT for TMC-derivatives, bifunctional nucleoside and triphosphate of the bifunctional nucleoside. The parent TMC-derivative had an $IC_{50}$ value of 13 nM. The data shows that the elaboration of the TMC-derivative with a 4-PEG linker, TMC-4PEG-OH (49 nM) results in a 4 fold lower potency. The addition of the d4U-NRTI moiety (d4U-4PEG-TMC) results in a 3 fold improvement in potency (16 nM). Finally, the preparation of the triphosphate of the d4U-4PEG-TMC nucleoside (d4U-TP-4PEG-TMC) results in the most potent compound, exhibiting 3 nM inhibition. This enhancement is a 4-5 fold improvement relative to the TMC-derivative and >500-fold improvement relative to d4T-TP. A similar set of experiments was carried out using a D24/D36mer primer-template determining potency to inhibit dGTP opposite template C (Table S1). Under these conditions, in which the d4U-4PEG-TMC and d4U-TP-4PEG-TMC would not be properly base paired, the $IC_{50}$ values of the TMC-derivative (11 nM) and TMC-4PEG-OH (29 nM) were similar, however, the $IC_{50}$ values for d4U-4PEG-TMC (35 nM) and d4U-TP-4PEG-TMC (38 nM) were reduced, indicating that the inhibition from the NRTI moiety is base specific. Further experiments examined the ability of the d4U-TP-4PEG-TMC to be incorporated into the radiolabeled D23/D36mer primer opposite template A in the absence of dTTP or the D24/D36 primer-template opposite template C in the absence of dGTP. The gel in FIG. 7 demonstrates the formation of an elongated primer chain terminated with the bifunctional monophosphate (D23-BifMP) with the D23/36mer primer-template but not the D24/36mer primer-template in a base specific manner requiring Mg$^{++}$ as as a divalent metal ion. This is the first time the TP of a NRTI-linker-NNRTI has been prepared & evaluated at a biochemical level.

TABLE S1

Steady-state inhibition of HIV-1 RT by bifunctional compounds and derivatives.

|  | $IC_{50}$ correct base pair (nM) | $IC_{50}$ incorrect base pair (nM) |
| --- | --- | --- |
| TMC derivative, D | 13 | 11 |
| TMC-4PEG-OH, E | 49 | 29 |
| d4U-4PEG-TMC, 1b | 16 | 35 |
| d4U-TP-4PEG-TMC, 1c | 3 | 38 |

Figure 7:
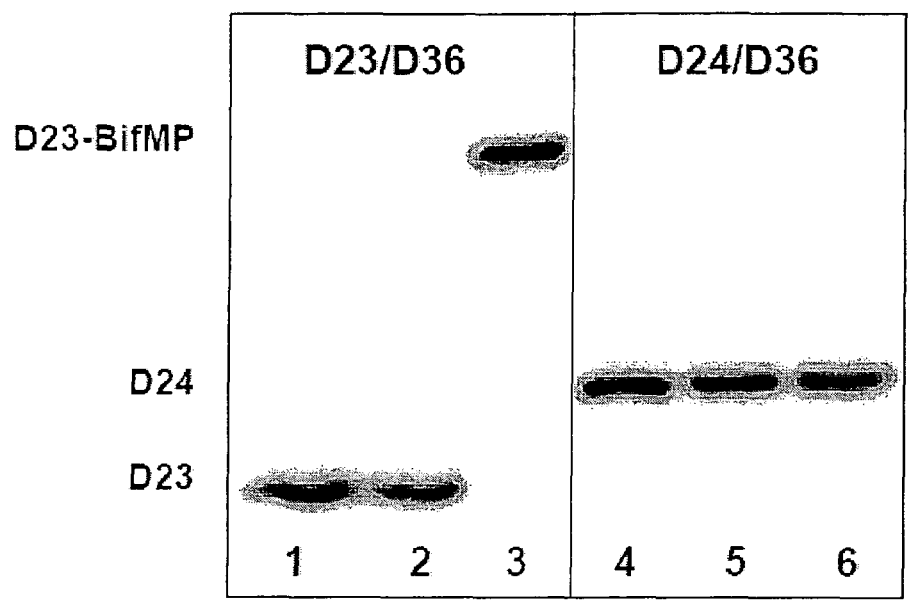
FIG. 7 shows that incorporation of d4UTP-4PEG-TMC by HIV-1 RT is base specific. Incubating d4UTP-4PEG-TMC, primer/template, and RT for 30 min. results in incorporation of the bifunctional-TP when using a primer for "T" incorporation opposite template A (lane 3), whereas a primer for "G" incorporation opposite template C yields no product (lane 6). Note the unique migration of the bifunctional MP elongated primer versus D24 (D23-dTMP). Controls for both primer/templates include 0 time points (lanes 1 and 4) and incubation for 30 min with no Mg$^{++}$ (lanes 2 and 5).

FIG. 7 shows that incorporation of d4UTP-4PEG-TMC by HIV-1 RT is base specific. Incubating d4UTP-4PEG-TMC, primer/template, and RT for 30 min. results in incorporation of the bifunctional-TP when using a primer for "T" incorporation opposite template A (lane 3), whereas a primer for "G" incorporation opposite template C yields no product (lane 6). Note the unique migration of the bifunctional MP elongated primer versus D24 (D23-dTMP). Controls for both primer/templates include 0 time points (lanes 1 and 4) and incubation for 30 min. with no Mg$^{++}$ (lanes 2 and 5).

Figure 8:
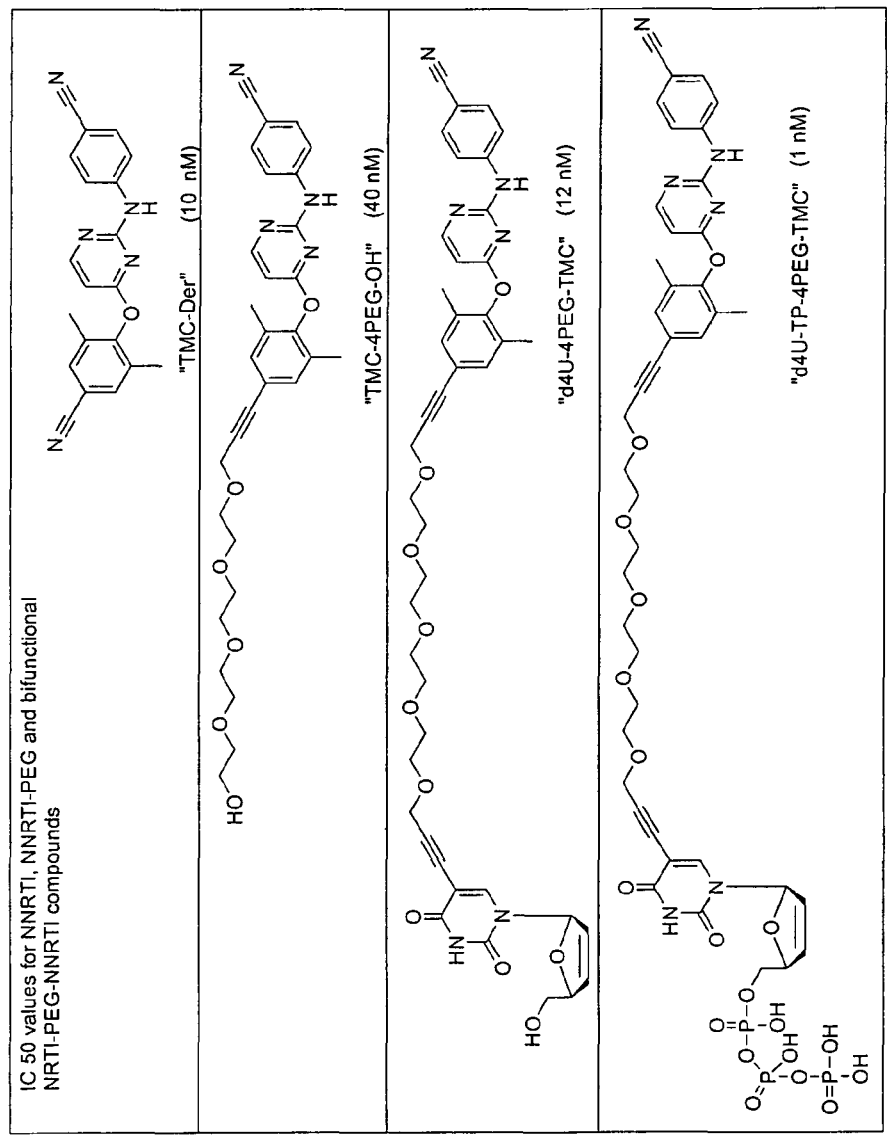
FIG. 8 shows the inhibition of reverse trascriptase by several compounds, including the bifunctional triphosphate (NRTI porition of molecule contains triphosphate group), which evidences substantially enhanced inhibitory activity.

FIG. 8 shows that a phosphorylated bifunctional compound according to the present invention is significantly more active than other compounds of similar, though limited structure.

EXAMPLES

Materials and Methods

Unless stated otherwise, reactions were performed in oven-dried glassware under a nitrogen atmosphere (house nitrogen, dried with Drierite® and KOH) using dry, deoxygenated solvents (distilled or passed over a column of activated alumina). 2-Thiouracil and 4-aminobenzonitrile were purchased from the Sigma-Aldrich Chemical Company and used as received. The key starting material, 4-(4-chloro-pyrimidin-2-ylamino) benzonitrile 2 was synthesized according to literature procedures (Ludovici, et al. *Bioorg. Med. Chem. Lett.* 2001, 11, 2235). Sephadex ion-exchange (DEAE) adsorbent was purchased from Sigma, while 4-iodo-2,6-dimethylphenol (Chabrier, et al., *C. R. Acad. Sc.*, 1957, 245, 174-175), 2-(2-(2-(2-(prop-2-ynyloxy)ethoxy)ethoxy)ethoxy)ethanol (Veciana, et al., *Synthesis*, 1992, 1164) and 5-iodo-5'-benzoyl-d4U (Mansuri, et al., *Bioorg. Med. Chem. Lett.*, 2007, 17, 2614-2617) were also prepared according to literature procedures. All reactions were magnetically stirred and monitored by thin-layer chromatography. Thin-layer chromatography (TLC) was performed using E. Merck silica-gel 60 F254 pre-coated plates (0.25 mm) or RediSep amine-functionalized silica-gel containing a 254 nm fluorescent indicator for the triphosphate synthesis, and visualized by UV fluorescence quenching, or Hanessian staining. Except for the triphosphate synthesis, traditional Flash-Chromatography and a CombiFlash Companion system were used for all of the separations using normal phase silica-gel utilizing repackable columns with 35-60 micron average particle size (230-400 mesh). The triphosphate synthesis purification was carried out on DEAE Sephadex with increasing percentages of aq. TEAB (1M, triethylammonium bicarbonate)/$H_2O$ mixtures as the mobile phase. TLC for the latter utilized TEAB/MeOH=6:4 on RediSep amine-functionalized plates. $^1H$ and $^{13}C$ NMR spectra were recorded on a Bruker Avance DPX (at 500 MHz and 400 MHz, respectively) in solvents CDCl$_3$ and MeOH-d$_4$, with the resonances for CDCl$_3$ taken as δ 7.24 ppm for $^1H$ and δ 77.0 ppm for $^{13}C$, and for MeOH-d$_4$ as δ 3.30 ppm for $^1H$ and δ 49.0 ppm for $^{13}C$ to serve as internal references (Cambridge Isotope Labs, Inc.). The data for $^1H$ NMR spectra are reported as follows: chemical shift (δ ppm) (multiplicity, coupling constant (Hz), integration). Those for $^{13}C$ NMR spectra are reported in terms of chemical shifts to one significant figure relative to the solvent references as described above. High resolution mass spectra were obtained from the Keck Biotechnology Resource Laboratory, Yale University.

dTTP and dGTP were purchased from GE Biosciences. Oligonucleotide primers and template were synthesized and purified using 20% denaturing gel-electrophoresis. Primers and template used in this study are as follows: D23 (5'-TCA GGT CCC TGT TCG GGC GCC AC-3'), D24 (5'-TCA GGT CCC TGT TCG GGC GCC ACT-3'), and D36 (5'-TCT CTA GCA GTG GCG CCC GAA CAG GGA CCT GAA AGC-3'). Labeling and annealing of primer/templates were performed as described previously. Murakami, et al., *J. Biol. Chem.* 2003, 278, 36403-36409.

Expression and Purification of HIV-1 RT.

C-terminal histidine tagged heterodimeric p66/p51 wild-type HIV-1 RT was expressed and purified as described previously (Kerr and Anerson, *Biochemistry*, 1997, 36, 14064-14070) using a clone generously provided by Stephen Hughes, Paul Boyer, and Andrea Ferris (Fredrick Cancer Research and Development Center, Fredrick, Md.).

$IC_{50}$ determination.

8 nM RT (active sites based on pre-steady state active site determination) was pre-incubated for at least 15 minutes with 1 μM 5'-labeled primer/template prior to mixing with appropriate concentrations of inhibitor and allowed to incubate for a minimum of 15 additional minutes on ice. DMSO concentrations were kept constant at less than 2%. DMSO alone was added as a no inhibitor control for each set of experiments. Reactions were initiated with the addition of 5 μM dNTP and 10 mM $MgCl_2$ and were quenched after 15 minutes at 37° C. with 0.3 M EDTA. All concentrations represent final concentrations after mixing. Reaction products were subjected to 20% denaturing polyacrylamide gel-electrophoresis and quantitated on a Bio-Rad Molecular Imager FX. Product formation was plotted as a function of inhibitor concentration and fitted to a hyperbola to generate $IC_{50}$ curves. $IC_{50}$ values are defined as the concentration of inhibitor that inhibits steady-state single nucleotide incorporation by 50%.

Incorporation Assays.

Incorporation experiments were performed under single turnover conditions; 50 μM d4U-TP-4PEG-TMC and 10 mM $MgCl_2$ were mixed with 250 nM RT (active sites) and 50 nM 5'-labeled primer/template to initiate the reaction. Negative controls were performed under identical conditions without $MgCl_2$. The reaction was allowed to proceed for 30 minutes at 37° C., after which the reaction was quenched with 0.3 M EDTA. Reaction products were subjected to 20% denaturing polyacrylamide gel-electrophoresis and analyzed on a Bio-Rad Molecular Imager FX.

High-Pressure Liquid Chromatography of d4U-TP-4PEG-TMC 1c.

d4U-TP-4PEG-TMC was further analyzed by HPLC using a DNA Pac PA-100 analytical column (Dionex, Sunnyvale, Calif.) using the following conditions: mobile phase A, 0.05 M triethylammonium bicarbonate (TEAB), pH 8.0; mobile phase B, 0.5 M TEAB, pH 8.0. Mobile phase flow rate was 1 mL/min using a gradient of 100% A to 50% A/50% B for ten minutes and then to 100% B for five minutes. Mobile phase flow rate was 1 mL/min using a gradient of 100% A to 50% A/50% B for ten minutes and then to 100% B for five minutes. Absorbance was measured at 260 nm.

Molecular Modeling of d4U-4PEG-TMC bound to HIV-1 RT/Template:Primer.

Since there is no crystal structure of RT complexed with both a NRTI and a NNRTI, a model was created starting from the crystal structures of the RT template:primer complex from Huang et al. (*Science*, 1998, 282, 1669-1679) (PDB entry 1rtd) and the Das et al. complex of the TMC120-R147681 NNRTI (Das, et al., *J. Med. Chem.* 2004, 47, 2550-2560) (PDB entry 1s6q). First, both of these files were read into the UCSF Chimera program (Pettersen, et al., *J. Comput. Chem.*, 2004, 25, 1605-1612) and superimposed using the matchmaker utility. A composite protein was then created by combining residues 1a-92a, 108a-178a, 241a-554a, 3b-249b, the template, primer and the 4 $Mg^{2+}$ ions from 1rtd and 93a-107a, 179a-240a, and the ligand from 1s6q.

The initial 3D structure of the bifunctional ligand bf4 was created by drawing it in ChemDraw and energy minimization using the MM2 force field in Chem3D and writing as a PDB file. After reading this structure in Chimera, the nucleotide end of this molecule was superimposed to the dNTP of the composite protein created above, and a few of the dihedrals on the polyethylene glycol linker were manually changed to g+ or g− to superimpose as best as possible the NNRTI end to the TMC120 crystallographic ligand. The sidechain torsions □1 and □2 of Y188a were adjusted by −30 and +30° respectively to avoid a severe steric clash. Finally, the crystallographic dNTP and TMC120 were then removed and the resulting complex exported as a PDB file.

The creation of the model was completed by reading the PDB files created by Chimera in Schrödinger's Maestro 7.5 and adding the hydrogen atoms needed at protonation states appropriate to pH=7. The following set of energy minimizations were sequentially run with the Impact program using the OPLS_2001 force field with a distance-dependent dielectric δ=4r, a 12 Å cutoff for non-bonded interactions, and the steepest descent algorithm. First, the newly created ligand and the segments of the protein chains originally from the 1s6q structure (93a-107a, 179a-240a) as well as all the residues within 4 Å of those were allowed to moved while the rest were kept fixed at their original positions during a 100-step optimization during which the total energy of the system decreased from $6.1 \times 10^{14}$ to 927.0 kcal/mol. The resulting structure was checked for consistence, and a second run of 300 steps was restarted form this point using the same degrees of freedom during which the energy decreased further to −187.2 kcal/mol. The entire system was then allowed to relax for successive optimizations of 100 and 300 steps reduced the total energy from 8,490.5 to −3,398.0 kcal/mol. The $C^\alpha$ rms deviation of the final structure to the initial 1rtd is only 0.27 Å which shows that there was relative little distortion created by the process.

Experimental

4-[4-(4-iodo-2,6-dimethylphenoxy)pyrimidin-2-ylamino]benzonitrile (3)

3

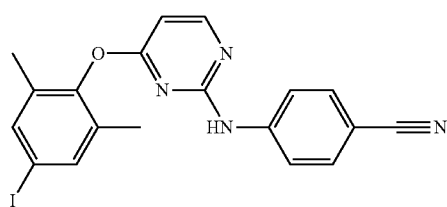

A mixture of 4-(4-chloro-pyrimidin-2-ylamino)benzonitrile (Ludovici, et al. ibid) 2 (600.0 mg, 2.60 mmol), 4-iodo-2,6-dimethylphenol (Chabrier, et al., Ibid) (838.0 mg, 3.38 mmol) and cesium carbonate (2.20 g, 6.76 mmol) in dry DMF (12 mL) was heated to 90° C. (Zhang, et al., *Tetrahedron Lett.*, 2002, 43, 8235-8239). After 3 hours, TLC (EtOAc/hexane=50:50) revealed a more polar product and consumption of compound 2. The mixture was poured into water (100 mL) and the product extracted into EtOAc (3×50 mL). The combined extracts were washed with brine (50 mL) followed by water (2×50 mL), and then dried over ($Na_2SO_4$) and the solvent evaporated in vacuo to furnish a residue that was subjected to silica-gel column chromatography using EtOAc/hexane (50:50) as eluent to produce 3 as a white solid (982.0 mg, 2.22 mmol, 85%).

$^1$H-NMR ($CDCl_3$, 500 MHz): δ (ppm) 8.31 (d, J=6.0 Hz, 1H), 7.48 (s, 2H), 7.42 (d, J=8.5 Hz, 1H), 7.36 (d, J=8.5 Hz, 1H), 7.31 (s, 1H, NH), 6.47 (d, J=6.0 Hz, 1H), 2.06 (s, 6H); $^{13}$C-NMR ($CDCl_3$, 500 MHz): δ (ppm) 168.9, 159.7, 159.1, 149.9, 143.3, 137.5, 133.4, 133.1, 119.3, 118.1, 104.7, 99.5, 89.9, 16.0; HRMS ($EI^+$) m/z calc'd for $C_{19}H_{15}IN_4O$ $[M+H]^+$: 443.0363. Found 443.0357.

4-(4-{4-[3-(2-{2-[2-(2-Hydroxy-ethoxy)-ethoxy]-ethoxy}-ethoxy)-prop-1-ynyl]-2,6-dimethyl-phenoxy}-pyrimidin-2-ylamino)-benzonitrile (4)

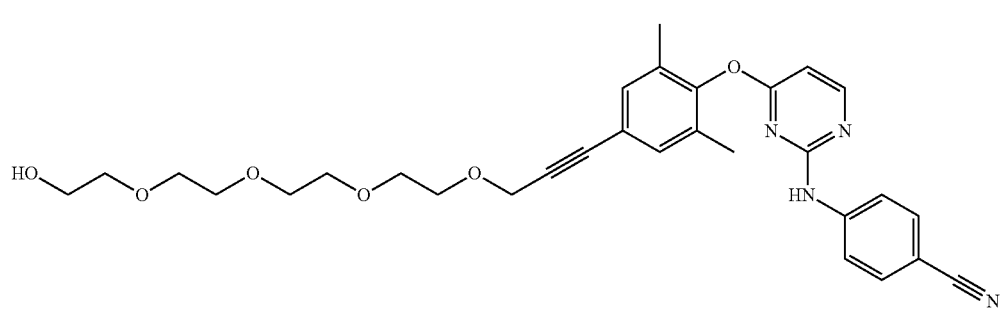

To a deoxygenated solution of iodopyrimidine 3 (494 mg, 1.12 mmol) and 2-(2-(2-(2-(prop-2-ynyloxy)ethoxy)ethoxy)ethoxy)ethanol (Veciani, et al., Ibid.) (780 mg, 3.36 mmol) in dry DMF (1.5 mL) and dry THF (3.0 mL) were added successively dry triethylamine (562.0 mg, 5.55 mmol, 0.80 mL), copper (1) iodide (105.7 mg, 0.56 mmol), and tetrakis(triphenylphosphine)palladium (0) (128.3 mg, 0.11 mmol). The reaction mixture was stirred at 25° C. under a nitrogen atmosphere for 3 hours after which TLC (DCM/methanol=3:97) revealed a more polar product and consumption of starting material 3. The mixture was poured into EDTA solution (20 mL, 5%) and the organic product extracted into EtOAc (3×50 mL). The combined organic extracts were washed with brine (20 mL), dried over $Na_2SO_4$ and the solvent evaporated in vacuo to furnish a residue that was subjected to silica-gel column chromatography using DCM/MeOH (95:5) as eluent to produce 4 as a light-brown oil (522.0 mg, 0.956 mmol, 85%).

$^1$H-NMR (CD$_3$OD, 400 MHz): δ (ppm) 8.37 (d, J=5.6 Hz, 1H) 7.44 (d, J=9.2 Hz, 2H), 7.35 (d, J=9.2 Hz, 2H), 7.27 (s, 2H), 6.60 (d, J=5.6, 1H), 4.46 (s, 2H), 3.71-3.79 (m, 4H), 3.53-3.66 (m, 12H), 2.08 (s, 6H); $^{13}$C-NMR (CDCl$_3$, 500 MHz): δ (ppm) 169.1, 159.3, 150.0, 143.4, 133.0, 132.1, 131.2, 120.3, 119.3, 118.1, 104.6, 99.5, 85.6, 85.1, 72.5, 70.7, 70.6, 70.6, 70.5, 70.4, 69.2, 61.8, 59.2, 16.3; HRMS (EI$^+$) m/z calc'd for $C_{30}H_{34}N_4O_6$ [M+H]$^+$: 547.2551. Found 547.2528.

Dry triethylamine (278 mg, 2.75 mmol, 0.4 mL) followed by p-toluenesulfonyl chloride (349.0 mg, 1.83 mmol) and 4-dimethylaminopyridine (11.2 mg, 0.009 mmol) were added to alcohol 4 (500.0 mg, 0.92 mmol) dissolved in dry dichloromethane (5 mL). The reaction was left stirring for 3 h at rt after which time TLC (DCM/MeOH=5:95) revealed a less polar product and consumption of starting material 4. The mixture was poured into saturated aq. sodium bicarbonate (20 mL) and extracted with dichloromethane (3×50 mL). The combined organic extracts were washed with brine (20 mL) and then dried (Na$_2$SO$_4$). Evaporation of the solvent in vacuo gave a light brown oil (658.0 mg), which was taken to the next step directly by adding it to a solution of propargyl alcohol (526 mg, 9.39 mmol, 0.54 mL) dissolved in dry THF (5 mL) to which sodium hydride (375 mg, 60%, 9.39 mmol) had been added. The reaction mixture was heated to 60° C. for 3 hours after which time TLC (DCM/MeOH=5:95) indicated the formation of a more polar product and consumption of the intermediate. The mixture was poured into saturated aq. sodium bicarbonate (20 mL) and extracted with EtOAc (3×50 mL), the combined organic extracts washed with brine (20 mL) and then dried (Na$_2$SO$_4$). Evaporation of the solvent in vacuo gave a residue that was subjected to column chromatography on silica-gel using DCM/MeOH mixtures to furnish 5 as a light-yellow oil (493.0 mg, 0.84 mmol, 92% for the two steps).

$^1$H-NMR (CDCl$_3$, 500 MHz): δ (ppm) 8.28 (d, J=6.0 Hz, 1H), 8.05 (s, 1H, NH), 7.35 (m, 4H), 7.18 (s, 2H), 6.44 (d, J=6.0 Hz, 1H), 4.38 (s, 2H), 4.11 (d, J=2.5 Hz, 2H), 3.72-3.67 (m, 4H), 3.66-3.58 (m, 12H), 2.37 (t, J=2.5 Hz, 1H), 2.03 (s, 6H); $^{13}$C-NMR (CDCl$_3$, 500 MHz): δ (ppm), 168.9, 159.4, 159.1, 149.9, 143.5, 132.8, 131.9, 131.1, 120.0, 119.2, 118.1, 104.2, 99.2, 85.5, 84.9, 79.5, 74.4, 70.5, 70.4, 70.4, 70.4, 70.3, 70.2, 69.1, 68.9, 59.0, 58.2, 16.1; HRMS (EI$^+$) m/z calc'd for $C_{33}H_{36}N_4O_6Na$ [M+Na]$^+$: 607.2527. Found 607.2500.

4-(4-(4-(3-(2-(2-(2-(2-(prop-2-ynyloxy)ethoxy)ethoxy)ethoxy)prop-1-ynyl)-2,6-dimethylphenoxy)pyrimidin-2-ylamino)benzonitrile (5)

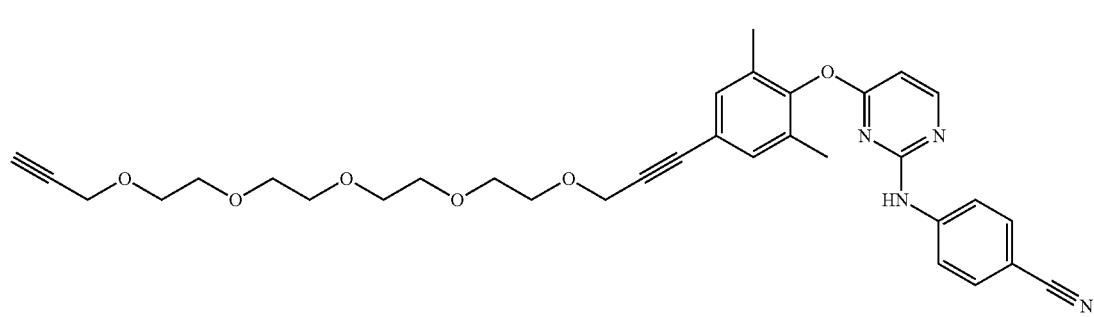

Benzoyld4U-propynyl-4-PEG-propynyl-TMC-120
(1a)

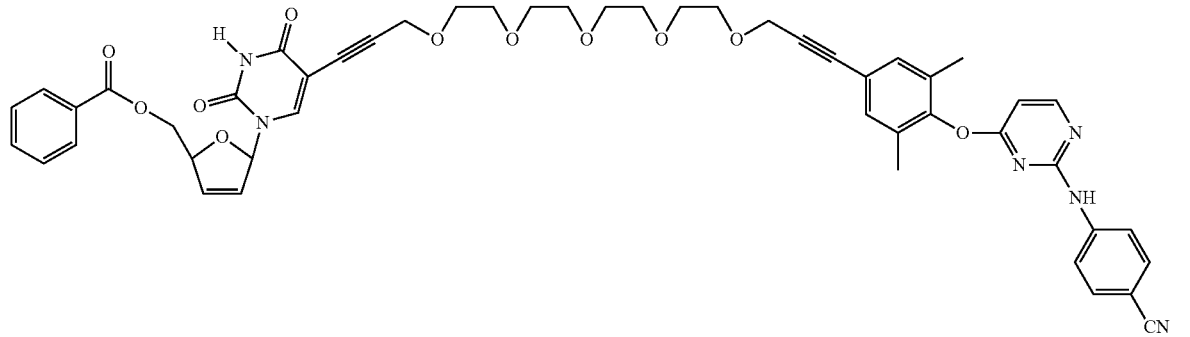

A mixture of (tetrakis)triphenylphosphinepalladium (0) (30.0 mg, 0.026 mmol) and copper (I) iodide (30.0 mg, 0.16 mmol) was added rapidly to a solution of 5-iodo-5'-benzoyl-d4U (Mansuri, et al., Ibid.) (110 mg, 0.25 mmol) and alkyne 6 (99.0 mg, 0.17 mmol) in a degassed mixture of THF and DMF (6 ml, 2:1) at room temperature under nitrogen. TLC indicated reaction to a more polar product to be complete after 3 hours with complete consumption of alkyne. Work-up involved adding EDTA solution (20 ml, 5%) and extracting the product into EtOAc (3×50 ml). Drying ($Na_2SO_4$) and evaporation of solvent followed by column chromatography of the residue on silica-gel using EtOAc/hexane mixtures as eluent furnished the bifunctional compound 7 (91.0 mg, 59%).

$^1$H-NMR $CDCl_3$, 500 MHz): δ (ppm) 11.82 (1H, s), 8.95 (1H, s), 8.42 (1H, d, J=5.7 Hz), 7.99 (2H, m), 7.67 (1H, s), 7.56 (1H, m), 7.43 (m, 2H), 7.32 (m, 4H), 7.22 (s, 2H), 6.94 (m, 1H), 6.47 (d, J=5.7 Hz, 1H), 6.39 (m, 1H), 5.96 (m, 1H), 5.19 (m, 1H), 4.67 (dd, J=4.5, 10.0 Hz, 1H), 4.49 (dd, J=3.0, 10.0 Hz, 1H), 4.43 (s, 2H), 4.20 (s, 2H), 3.58-3.80 (m, 16H), 2.06 (s, 6H); $^{13}$C-NMR ($CDCl_3$, 500 MHz): δ (ppm 169.2, 166.2, 162.2, 159.0, 158.9, 150.3, 150.1, 143.6, 142.5, 133.7, 133.4, 132.8, 132.1, 131.2, 129.7, 129.1, 128.7, 126.8, 120.2, 119.5, 118.2, 104.2, 100.2, 99.0, 90.6, 90.1, 85.6, 85.2, 85.1, 77.0, 70.6, 70.5, 70.5, 70.5, 70.4, 70.3, 69.2, 69.2, 65.0, 59.2, 59.0, 16.2; HRMS (EI$^+$) m/z calc'd for $C_{49}H_{48}N_6O_{11}$ [M+H]$^+$: 897.3453. Found 897.3464.

d4U-propynyl-4-PEG-propynyl-TMC-120 (1b)

To a solution of benzoate 1a (38.0 mg, 0.042 mmol) dissolved in methanol (3 mL) at 0° C. was added a solution of sodium methoxide in methanol (0.5 M, 0.1 mL). After 2 h, the solution was allowed to warm to rt. Once TLC indicated the complete consumption of starting material, acetic acid was added (3.0 mg, 0.05 mmol) and the methanol removed on the rotoevaporator. The residue was immediately chromatographed on silica-gel using EtOAc/MeOH mixtures to obtain nucleoside 1b (31.5 mg, 94%) as a colourless oil.

$^1$H-NMR $CDCl_3$, 500 MHz), δ (ppm) 11.54 (br.s, 1H), 8.88 (br.s, 1H), 8.38 (d, J=5.2 Hz, 1H), 8.34 (s, 1H), 7.33 (m, 4H), 7.22 (s, 2H), 6.98 (m, 1H), 6.47 (d, J=5.2 Hz, 1H), 6.34 (d, J=5.8 Hz, 1H), 5.82 (d, J=5.8 Hz, 1H), 4.94 (m, 1H), 4.44 (s, 2H), 4.32 (s, 2H), 3.94 (dd, J=3.0, 11.2 Hz, 1H), 3.84 (dd, J=2.0, 11.2 Hz, 1H), 3.60-3.80 (m, 16H), 3.48 (brs, 1H, OH), 2.06 (s, 6H); $^{13}$C-NMR ($CDCl_3$, 500 MHz) δ (ppm) 169.2, 162.4, 159.1, 158.9, 150.5, 150.2, 145.2, 143.6, 135.0, 132.8, 132.1, 131.3, 126.0, 120.1, 119.5, 118.3, 104.2, 99.4, 99.0, 90.1, 89.1, 87.7, 85.7, 85.0, 77.9, 70.5, 70.5, 70.5, 70.4, 70.4, 70.3, 69.2, 69.0, 62.7, 59.2, 59.2, 16.3; HRMS (EI$^+$) m/z calc'd for $C_{42}H_{44}N_6O_{10}$ [M+H]$^+$: 793.3191. Found 793.3204.

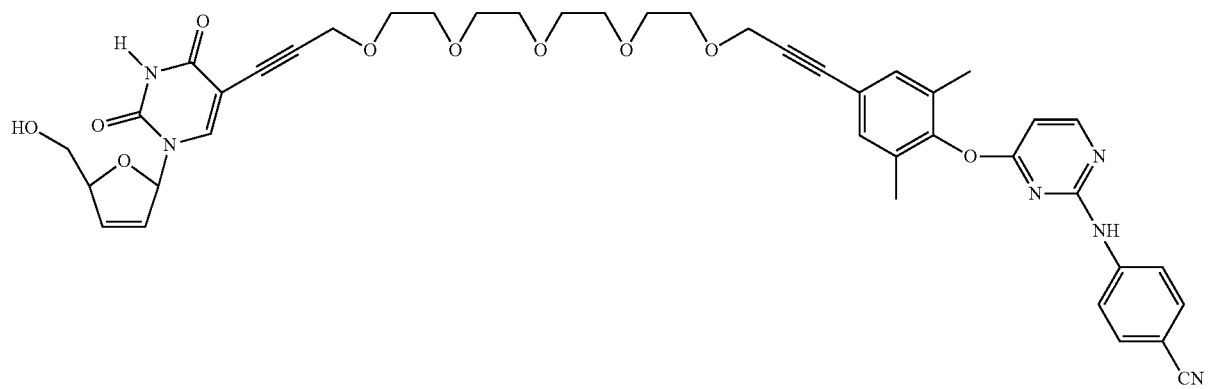

d4U-propynyl-4-PEG-propynyl-TMC-120
Triphosphate (1c)

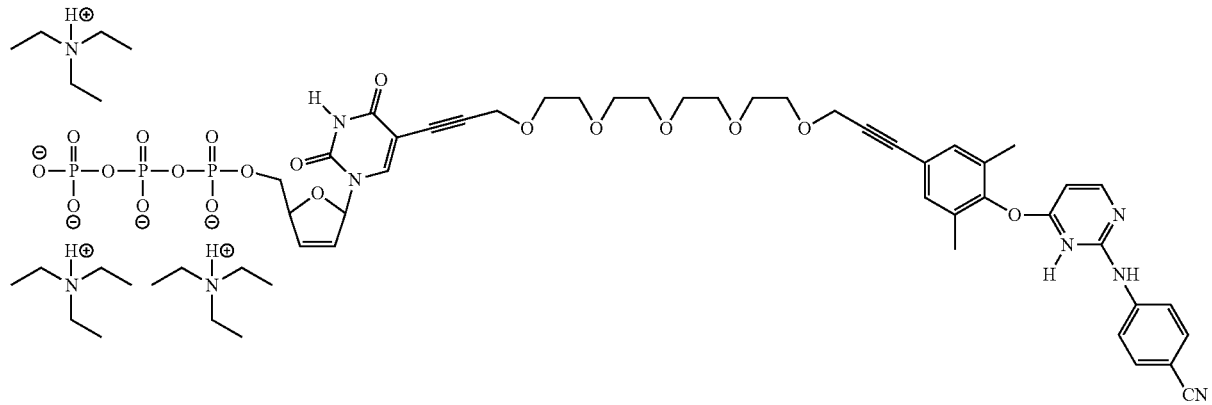

The bifunctional nucleoside 1b (95.0 mg, 0.120 mmol) was dissolved in a 1:1 mixture of DMF/Pyridine (1.0 ml) and the flask cooled to −20° C. 2-Chloro-1,3,2-benzodioxaphosphorin-4-one (Eckstein and Ludwig, *J. Org. Chem.*, 1989, 54, 631)(30.0 mg, 0.148 mmol) dissolved in THF (0.5 mL) was added slowly and the reaction left to warm to rt. After 60 mins, bis(tributylammonium) pyrophosphate (92.0 mg, 0.168 mmol) in DMF (0.5 ml) was added followed by triethylamine (0.5 ml) and the solution left stirring for 1 h. $I_2$ (43.0 mg, 0.170 mmol) dissolved in pyridine/water (2 ml, 98:2) was then added, and the solution left stirring for 15 min before being quenched by aq. $Na_2S_2O_3$ (0.5 M, 0.5 ml). TEAB (1 M, 3.0 ml) was immediately added and the solution left stirring for 2 h at rt. The solution was then evaporated to dryness before being chromatographed on a Sephadex ion-exchange (DEAE) column (3.0 g) using aq. TEAB as the mobile phase. The bifunctional triphosphate eluted at around 0.6 M. Fractions identified from tlc (amine-impregnated silica-gel plates using TEAB/MeOH=3.5/6.5) were combined and the solvent evaporated. Following several additions of methanol with pumping, the tris(tiethylammonium) triphosphate 1c (60.0 mg, 0.045 mmol, 37%) was obtained as a colorless oil.

$^1$H-NMR (CD$_3$OD, 500 MHz): δ (ppm) 8.32 (m, 1H), 7.78 (s, 1H), 7.43 (m, 2H), 7.33 (m, 2H), 7.23 (s, 2H), 6.85 (m, 1H), 6.55 (m, 2H), 5.88 (m, 1H), 5.02 (m, 1H), 4.42 (s, 2H), 4.32 (s, 2H), 4.12 (m, 2H), 3.54-3.74 (m, 16H), 3.13 (brs, 18H), 2.04 (s, 6H), 1.25 (brs, 27H); $^{13}$C-NMR (CD$_3$OD, 75 MHz) δ (ppm): 170.4, 164.1, 161.2, 160.8, 151.8, 151.6, 145.9, 145.4, 136.6, 133.7, 133.1, 132.8, 126.5, 121.5, 120.4, 119.6, 104.6, 100.5, 100.1, 91.8, 90.9, 87.5, 86.6, 86.0, 78.4, 71.5, 71.5, 71.5, 71.5, 71.5, 71.4, 70.2, 70.2, 68.4, 59.8, 59.7, 47.2, 16.4, 9.1; $^{31}$P-NMR (CD$_3$OD, 202.4 MHz): δ (ppm) −8.9 (d, J=20.2 Hz), −9.8 (d, J=20.2 Hz), −22.1 (t, J=20.2 Hz); HRMS (EI$^+$) m/z calc'd for the tetraphosphoric acid $C_{42}H_{46}N_6O_{19}P_3$ [M−H]$^+$: 1031.2036. Found 1031.2035.

Biological Activity

Cell Culture—

Antiviral activity and cellular toxicity were determined using the MTT colorimetric method. See, Mosmann, *J Immunol Methods*, 1983. 65(1-2): p. 55-63 and Pannecouque, et al., *Nat Protoc*, 2008. 3(3): p. 427-34. MT-2 cells (See, Haertle, et al., *J Biol Chem*, 1988. 263(12), p. 5870-5 and Harada, et al., *Science*, 1985. 229(4713): p. 563-6) at a concentration of 1×10$^5$ cells per millilitre were infected with wild-type HIV IIIB (See, Popovic, et al., *Lancet*, 1984. 2(8417-8418): p. 1472-3, Popovic, et al., *Science*, 1984, 224(4648): p. 497-500 and Ratner, et al., *Nature*, 1985, 313(6000): p. 277-84) at a multiplicity of infection (MOI) of 0.1. Infected and mock-infected cells were incubated in growth medium (RPMI 1640, 10% dFBS, kanamycin) for 5 days with varying concentrations of each compound being tested in triplicate in a 96-well plate. MTT (thiazolyl blue tetrazolium bromide), a cell-permeable tetrazolium dye was then added to each well. Active mitochondria reduce the yellow tetrazolium salt to a blue formazan precipitate. After 5 h, stop solution (86% isopropanol, 4% NP-40, 10% $H_2O$, and 0.3% concentrated HCl) was added to lyse the cells and stop the reaction. The plates were gently shaken gently overnight on a horizontal rotator, and quantitated the following morning. Cell viability was measured spectrophotometrically by quantifying the amount of purple precipitate via determining the absorbance at 595 nM using a Finstruments microplate reader. The average of these triplicate samples was then plotted versus inhibitor concentration to generate dose-response curves. The 50% effective concentration (EC$_{50}$) and 50% cytotoxic concentration (CC$_{50}$) of the compounds were defined as the concentrations required to inhibit viral replication and to reduce the number of viable cells by 50%, respectively. Positive controls were done during each set of experiments using d4T and the appropriate parent NNRTI (HI-236 or TMC-derivative). Data were quantitated using KaleidaGraph (Synergy Software). See FIGS. 9A-C. The compound according to the present invention evidenced significant activity in the assay.

REFERENCES

1. Jasny, B. R., *AIDS* 1993: *Unanswered questions*. Science, 1993. 260: p. 1219.
2. De Clercq, E., *Toward Improved Anti-HIV Chemotherapy: Therapeutic Strategies for Intervention with HIV Infections*. Journal of Medicinal Chemistry, 1995. 38: p. 2491-2517.
3. De Clercq, E., *Antiviral Therapy for Human Immunodeficiency Virus Infections*. Clinical Microbiology Reviews, 1995. 8: p. 200-239.

4. Riddler, S. A., R. E. Anderson, and J. W. Mellors, *Antiretroviral Activity of Stavudine (D4T)*. Antiviral Research, 1995. 27: p. 189-203.
5. Clumeck, N., *Current use of anti-HIV drugs in AIDS. [Review]*. Journal of Antimicrobial Chemotherapy, 1993. 32 Suppl A: p. 133-138.
6. van Leeuwen, R., et al., *Evaluation of safety and efficacy of 3TC (lamivudine) in patients with asymptomatic or mildly symptomatic human immunodeficiency virus infection: a phase I/II study*. Journal. of. Infectious. Diseases., 1995. 171: p. 1166-1171.
7. Gu, Z., et al., *Mutated K65R recombinant reverse transcriptase of human immunodeficiency virus type 1 shows diminished chain termination in the presence of 2',3'-dideoxycytidine 5'-triphosphate and other drugs*. Proc Natl Acad Sci USA, 1995. 92: p. 2760-2764.
8. Faraj, A., et al., *Inhibition of human immunodeficiency virus type 1 reverse transcriptase by the 5'-triphosphate beta enantiomers of cytidine analogs*. Antimicrobial Agents & Chemotherapy, 1994. 38: p. 2300-2305.
9. Coates, J. A., et al., *(-)-2'-deoxy-3'-thiacytidine is a potent, highly selective inhibitor of human immunodeficiency virus type 1 and type 2 replication in vitro*. Antimicrobial Agents & Chemotherapy, 1992. 36: p. 733-739.
10. van Leeuwen, R., et al., *The safety and pharmacokinetics of a reverse transcriptase inhibitor, 3TC, in patients with HIV infection: a phase I study*. AIDS, 1992. 6: p. 1471-1475.
11. Lin, T. S., et al., *Synthesis and biological evaluation of 2',3'-dideoxy-L-pyrimidine nucleosides as potential antiviral agents against human immunodeficiency virus (HIV) and hepatitis B virus (HBV)*. Journal of Medicinal Chemistry, 1994. 37: p. 798-803.
12. Cohen, J., *Aids Trials Ethics Questions Answered*. Science, 1997. 276: p. 520.
13. Kohlstaedt, L. A., et al., *Crystal structure at 3.5 A resolution of HIV-1 reverse transcriptase complexed with an inhibitor*. Science, 1992. 256: p. 1783-1790.
14. Huang, H., et al., *Structure of a covalently trapped catalytic complex of HIV-1 reverse transcriptase: implications for nucleoside analog drug resistance*. Science, 1998. 282: p. 1669-1675.
15. Jacobo-Molina, A., et al., *Crystal structure of human immunodeficiency virus type 1 reverse transcriptase complexed with double-stranded DNA at 3.0 A resolution shows bent DNA*. Proceedings of the National Academy of Sciences, USA, 1993. 90: p. 6320-6324.
16. Sarafianos, S. G., et al., *Structures of HIV-1 reverse transcriptase with pre-and post-translocation AZTMP-terminated DNA*. Embo J, 2002. 21(23): p. 6614-24.
17. Joyce, C. M. and T. A. Steitz, *Function and structure relationships in DNA polymerases. [Review]*. Annual. Review. of. Biochemistry, 1994. 63: p. 777-822.
18. Polesky, A. H., et al., *Identification of residues critical for the polymerase activity of the Klenow fragment of DNA polymerase I from Escherichia coli*. Journal of Biological Chemistry, 1990. 265: p. 14579-14591.
19. Johnson, K. A., *Conformational coupling in DNA polymerase fidelity. [Review]*. Annual Review of Biochemistry, 1993. 62: p. 685-713.
20. Kati, W. M., et al., *Mechanism and fidelity of HIV reverse transcriptase*. J. Biol. Chem., 1992. 267(36): p. 25988-25997.
21. Reardon, J. E., *Human immunodeficiency virus reverse transcriptase. A kinetic analysis of RNA-dependent and DNA-dependent DNA polymerization*. Journal of Biological Chemistry, 1993. 268: p. 8743-8751.
22. Hsieh, J. C., S. Zinnen, and P. Modrich, *Kinetic mechanism of the DNA-dependent DNA polymerase activity of human immunodificiency virus reverse transcriptase*. J. Biol. Chem., 1993. 268: p. 24607-24613.
23. Spence, R. A., et al., *Mechanism of inhibition of HIV-1 reverse transcriptase by nonnucleoside inhibitors*. Science, 1995. 267(17): p. 988-993.
24. Rittinger, K., G. Divita, and R. S. Goody, *Human immunodeficiency virus reverse transcriptase substrate-induced conformational changes and the mechanism of inhibition by nonnucleoside inhibitors*. Proc. Natl. Acad. Sci. U.S.A, 1995. 92(17): p. 8046-8049.
25. De Clercq, E., *The role of non-nucleoside reverse transcriptase inhibitors (NNRTIs) in the therapy of HIV-1 infection*. Antiviral Res., 1998. 38: p. 153-179.
26. Panganiban, A. and D. Fiore, *Ordered Interstrand and Intrastrand DNA Transfer During Reverse Transcription*. Science, 1988. 241: p. 1064-1069.
27. Gilboa, E., et al., *A Detailed Model of Reverse Transcription and Tests of Crucial Aspects*. Cell, 1979. 18: p. 93-100.
28. Kim, J. K., et al., *Evidence for a unique mechanism of strand transfer from the transactiviation response region of HIV-1*. J. Biol. Chem., 1997. 272: p. 16769-16777.
29. Peliska, J. A., et al., *Recombinant HIV-1 nucleocapsid protein accelerates HIV-1 reverse transcriptase catalyzed DNA strand transfer reactions and modulates RNase H activity*. Biochemistry, 1994. 33: p. 13817-13823.
30. Peliska, J. A. and S. J. Benkovic, *Mechanism of DNA strand transfer reactions catalyzed by HIV-1 reverse transcriptase*. Science, 1992. 258: p. 1112-1118.
31. You, J. C. and C. S. McHenry, *Human immunodeficiency virus nucleocapsid protein accelerates strandtransfer of the terminally redundant sequences involved in reverse transcription*. Journal. of. Biological. Chemistry., 1994. 269: p. 31491-31495.
32. Rodriguez-Rodriguez, L., et al., *Influence of human immunodeficiency virus nucleocapsid protein on synthesis and strand transfer by the reverse transcriptase in vitro*. J. Biol. Chem., 1995. 270: p. 15005-15011.
33. Arts, E. J. and M. A. Wainberg, *Preferential incorporation of nucleoside analogs after template switching during human immunodeficiency virus reverse transcription*. Antimicrobial Agents & Chemotherapy, 1994. 38: p. 1008-1016.
34. Arts, E. J., et al., *Mutating a region of HIV-1 reverse transcriptase implicated in tRNA (Lys-3) binding and the consequences for (-)-strand DNA synthesis*. J Biol Chem, 1998. 273(23): p. 14523-32.
35. Isel, C., et al., *Modified nucleotides of tRNA (3Lys) modulate primer/template loop-loop interaction in the initiation complex of HIV-1 reverse transcription*. J. Biol. Chem., 1993. 68: p. 25269-25272.
36. Isel, C., et al., *Initiation of reverse transcription of HIV-1: secondary structure of the HIV-1 RNA/tRNA (3Lys) (template/primer)*. J. Mol. Biol., 1995. 247: p. 236-250.
37. Rigourd, M., et al., *Inhibition of the initiation of HIV-1 reverse transcription by 3'-azido-3'-deoxythymidine. Comparison with elongation*. J Biol Chem, 2000. 275(35): p. 26944-51.
38. Marchand, B. and M. Gotte, *Site-specific footprinting reveals differences in the translocation status of HIV-1 reverse transcriptase: Implications for polymerase translocation and drug resistance*. J Biol Chem, 2003.
39. Isel, C., et al., *Specific initiation and switch to elongation of human immunodeficiency virus type 1 reverse transcription require the post-transcriptional modifications of primer $tRNA_3^{lys}$*. EMBO J., 1996. 15: p. 917-924.

40. Isel, C., et al., *Mutational analysis of the tRNA$_3^{Lys}$/HIV-1 RNA (primer/template) complex.* Nucl. Acids Res., 1998. 26: p. 1198-1204.
41. Haseltine, W. A., *Molecular biology of the human immunodeficiency virus type 1.* FASEB J., 1991. 5: p. 2349-2360.
42. Gorelick, R. J., et al., *The two zinc fingers in the human immunodeficiency virus type 1 nucleocapsid protein are not functionally equivalent.* Journal of Virology, 1993. 67: p. 4027-4036.
43. Sakaguchi, K., et al., *Identification of a binding site for the human immunodeficiency virus type 1 nucleocapsid protein.* Proc Natl Acad Sci USA, 1993. 90: p. 5219-5223.
44. South, T. L., et al., *C-terminal retroviral-type zinc finger domain from the HIV-1 nucleocapsid protein is structurally similar to the N-terminal zinc finger domain.* Biochemistry, 1991. 30: p. 6342-6349.
45. Darlix, J.-L., et al., *First glimpses at structure-functure relationships of the nucleocapsid protein of retroviruses.* J. Mol. Biol., 1995. 254: p. 523-537.
46. Ottmann, M., C. Gabus, and J. L. Darlix, *The central globular domain of the nucleocapsid protein of human immunodeficiency virus type 1 is critical for virion structure and infectivity.* Journal. of. Virology., 1995. 69: p. 1778-1784.
47. Tsuchihashi, Z. and P. O. Brown, *DNA strand exchange and selective DNA annealing promoted by the human immunodeficiency virus type 1 nucleocapsid protein.* Journal of Virology, 1994. 68: p. 5863-5870.
48. Berkowitz, R. D. and S. P. Goff, *Analysis of binding elements in the human immunodeficiency virus type 1 genomic RNA and nucleocapsid protein.* Virology, 1994. 202: p. 233-246.
49. Barat, C., et al., *Analysis of the interactions of HIV1 replication primer tRNA (Lys,3) with nucleocapsid protein and reverse transcriptase.* J. of Mol. Biol., 1993. 231: p. 185-190.
50. Lener, D., et al., *Involvement of HIV-1 nucleocapsid protein in the recruitment of reverse transcriptase into nucleoprotein complexes formed in vitro.* J. Biol. Chem., 1998. 273: p. 33781-33786.
51. Barat, C., et al., *HIV-1 reverse transcriptase specifically interacts with the anticodon domain of its cognate primer tRNA.* EMBO J., 1989. 8: p. 3279-3285.
52. Remy, E., et al., *The annealing of tRNA$_3^{Lys}$ to human immunodeficiency virus type 1 primer binding site is critically dependent on the NCp7 zinc fingers structure.* J. Biol. Chem., 1998. 273: p. 4819-4822.
53. Chan, B., et al., *Intra-tRNA distance measurements for nucleocapsid protein-dependent tRNA distance measurements for nucleocapsid protein-dependent tRNA unwinding during priming of HIV reverse transcription.* Proc. Natl. Acad. Sci. USA, 1999. 96: p. 459-464.
54. Ji, X., G. Klarmann, and B. D. Preston, *Effect of human immunodeficiency virus type 1 (HIV-1) nucleocapsid protein on HIV-1 reverse transcriptase activity in vitro.* Biochemistry, 1996. 35: p. 132-143.
55. DeStefano, J. J., J. Biol. Chem., 1996. 271: p. 16350-16356.
56. Wu, W., et al., J. Virol., 1996. 70: p. 7132-7142.
57. Tanchou, V., et al., *Formation of stable and functional HIV-1 nucleoprotein complexes in vitro.* J. Mol. Biol., 1995. 252: p. 563-571.
58. Druillennec, S., et al., *Evidence of interactions between the nucleocapsid protein NCp7 and the reverse transcriptase of HIV-1.* J. Biol. Chem., 1999. 274: p. 11283-11288.
59. Furman, P. A., et al., *The anti-hepatitis B virus activities, cytotoxicities, and anabolic profiles of the (−) and (+) enantiomers of cis-5-fluoro-1-[2-(hydroxymethyl)-1,3-oxathiolan-5-yl]cytosine.* Antimicrob. Agents Chemother., 1992. 36(12): p. 2686-2692.
60. Skalski, V., et al., *The biochemical basis for the differential anti-human immunodeficiency virus activity of two cis enantiomers of 2',3'-dideoxy-3'-thiacytidine.* Journal. of. Biological. Chemistry., 1993. 268: p. 23234-23238.
61. Chang, C. N., et al., *Biochemical pharmacology of (+)- and (−)-2',3'-dideoxy-3'-thiacytidine as anti-hepatitis B virus agents.* J. Biol. Chem., 1992. 267: p. 22414-22420.
62. Cammack, N., et al., *Cellular metabolism of (−) enantiomeric 2'-deoxy-3'-thiacytidine.* Biochemical Pharmacology, 1992. 43: p. 2059-2064.
63. Mely, Y., et al., *Spatial proximity of the HIV-1 nucleocapsid protein zinc fingers investigated by time-resolved fluorescence and fluorescence resonance energy transfer.* Biochemistry, 1994. 33: p. 12085-12091.
64. Coates, J. A., et al., *The separated enantiomers of 2'-deoxy-3'-thiacytidine (BCH 189) both inhibit human immunodeficiency virus replication in vitro.* Antimicrobial. Agents &. Chemotherapy., 1992. 36: p. 202-205.
65. Pauwels, R., et al., *Potent and selective inhibition of HIV-1 replication in vitro by a novel series of TIBO derivatives.* Nature, 1992. 343: p. 470-474.
66. Mellors, J. W., et al., *In vitro selection and molecular characterization of human immunodeficiency virus-1 resistant to non-nucleoside inhibitors of reverse transcriptase.* Molecular Pharmacology, 1992. 41: p. 446-451.
67. Frank, K. B., et al., *Kinetic interaction of human immunodeficiency virus type 1 reverse transcriptase with the antiviral tetrahydroimidazo[4,5,1-jk]-[1,4]-benzodiazepine-2-(1H)-thione compound, R82150.* Journal of Biological Chemistry, 1991. 266: p. 14232-14236.
68. Kopp, E. B., et al., *Steady state kinetics and inhibition of HIV-1 reverse transcriptase by a non-nucleoside dipyridodiazepinone, BI-RG-587, using a hetropolymeric template.* Nucleic Acids Research, 1991. 19: p. 3035-3039.
69. Shih, C.-K., et al., *Chimeric human immunodeficiency virus type 1/type 2 reverse transcriptases display reversed sensitivity to nonnucleoside analog inhibitors.* Proceedings of the National Academy of Sciences, USA, 1991. 88: p. 9878-9882.
70. Buckheit, R. W. J., et al., *Cell-based and biochemical analysis of the anit-HIV activity of combinations of 3'-azido-3'deoxythymidine and analogues of TIBO.* Antiviral Chem. Chemother., 1994. 5: p. 35-42.
71. Richman, D. D., et al., *BI-RG-587 is active against zidovudine-resistant human immunodeficiency virus type 1 and synergistic with zidovudine.* Antimicrob Agents Chemother, 1991. 35: p. 305-308.
72. De Clercq, E., *Non-nucleoside reverse transcriptase inhibitors (NNRTIs) for the treatment of human immunodeficiency virus type 1 (HIV-1) infections: Stratagies to overcome drug resistance development.* Medicinal Res. Rev., 1996. 16: p. 125-157.
73. Havlir, D., M. M. McLaughlin, and D. D. Richman, *A pilot study to evaluate the development of resistance to nevirapine in asyptomatic human immunodeficiency virus-infected patients with CD4 cell count of >500/mm$^3$: AIDS clinical trials group protocol 208.* J. Infect. Dis., 1995. 172: p. 1379-1383.
74. Lewis, W., et al., *Zidovudine induces molecular, biochemical, and ultrastructural changes in rat skeletal muscle mitochondria.* Journal. of. Clinical. Investigation., 1992. 89: p. 1354-1360.

75. Lewis, W., J. F. Simpson, and R. R. Meyer, *Cardiac mitochondrial DNA polymerase-gamma is inhibited competitively and noncompetitively by phosphorylated zidovudine.* Circulation. Research., 1994. 74: p. 344-348.
76. Lewis, W. and M. C. Dalakas, *Mitochondrial toxicity of antiviral drugs.* Nat Med, 1995. 1(5): p. 417-22.
77. Herzberg, N. H., et al., *Major growth reduction and minor decrease in mitochondrial enzyme activity in cultured human muscle cells after exposure to zidovudine.* Muscle. &. Nerve., 1992. 15: p. 706-710.
78. Parker, W. B. and Y. C. Cheng, *Mitochondrial Toxicity of Antiviral Nucleoside Analogs.* Journal of NIH Research, 1994. 6: p. 57-61.
79. Martin, J. L., et al., *Effects of antiviral nucleoside analogs on human DNA polymerases and mitochondrial DNA synthesis.* Antimicrobial. Agents &. Chemotherapy., 1994. 38: p. 2743-2749.
80. Medina, D. J., et al., *Comparison of mitochondrial morphology, mitochondrial DNA content, and cell viability in cultured cells treated with three anti-human immunodeficiency virus dideoxynucleosides.* Antimicrobial. Agents &. Chemotherapy., 1994. 38: p. 1824-1828.
81. Tsai, C.-H., et al., *Effect of anti-HIV 2'-b-fluoro-2',3'-dideoxynucleoside analogs on the cellular content of mitochondrial DNA and on lactate production.* Biochem. Pharmacol., 1994. 48: p. 1477-1481.
82. Chen, C. H., M. Vazquez-Padua, and Y. C. Cheng, *Effect of anti-human immunodeficiency virus nucleoside analogs on mitochondrial DNA and its implication for delayed toxicity.* Molecular Pharmacology, 1991. 39: p. 625-628.
83. Parker, W. B., et al., *Mechanism of inhibition of human immunodeficiency virus type 1 reverse transcriptase and human DNA polymerases a, b and g by the 5'-triphosphates of carbovir, 3'-azido-3'-deoxythymidine, 2',3'-dideoxyguanosine, and 3'-deoxythymidine. A novel RNA template for the evaluation of antiretroviral drugs.* Journal of Biological Chemistry, 1991. 266: p. 1754-1762.
84. Colacino, J. M., *Mechanisms for the anti-hepatitis B virus activity and mitochondrial toxicity of fialuridine (FIAU).* Antiviral Res., 1996. 29: p. 125-139.
85. Fried, M. W., et al., *FIAU, a new oral anti-viral agent, profoundly inhibits HBV DNA in patients with chronic hepatitis B.* Hepatoloty, 1992. 16: p. 127a.
86. Feng, J. Y., et al., *Insights into the Molecular Mechanism of Mitochondrial Toxicity by AIDS Drugs.* J. Biol. Chem, 2001. 276: p. 23832-7.
87. Johnson, A. A., et al., *Toxicity of antiviral nucleoside analogs and the human mitochondrial DNA polymerase.* J Biol Chem, 2001. 276(44): p. 40847-57.
88. Richman, D. D., *HIV Drug Resistance.* Annual Reviews in Pharmacology and Toxicology, 1993. 32: p. 149-164.
89. Ray, A. S., A. Basavapathruni, and K. S. Anderson, *Mechanistic studies to understand the progressive development of resistance in human immunodeficiency virus type 1 reverse transcriptase to abacavir.* J Biol Chem, 2002. 277(43): p. 40479-90.
90. Shah, F. S., et al., *Differential influence of nucleoside analog-resistance mutations K65R and L74V on the overall mutation rate and error specificity of human immunodeficiency virus type 1 reverse transcriptase.* J Biol Chem, 2000. 275(35): p. 27037-44.
91. Hsu, M., et al., *Higher fidelity of RNA-dependent DNA mispair extension by M184V drug-resistant than wild-type reverse transcriptase of human immunodeficiency virus type 1.* Nucleic Acids Res., 1997. 25(22): p. 4532-4536.
92. Rezende, L. F., W. C. Drosopoulos, and V. R. Prasad, *The influence of 3TC resistance mutation M184I on the fidelity and error specificity of human immunodeficiency virus type 1 reverse transcriptase.* Nucleic Acids Res., 1998. 26(12): p. 3066-3072.
93. Wainberg, M. A., et al., *Ehannced fidelity of 3TC-selected mutant HIV-1 reverse transcriptase.* Science, 1996. 271: p. 1282-1285.
94. Fisher, T. S., T. Darden, and V. R. Prasad, *Mutations proximal to the minor groove-binding track of human immunodeficiency virus type 1 reverse transcriptase differentially affect utilization of RNA versus DNA as template.* J Virol, 2003. 77(10): p. 5837-45.
95. Rezende, L. F., Y. Kew, and V. R. Prasad, *The effect of increased processivity on overall fidelity of human immunodeficiency virus type 1 reverse transcriptase.* J Biomed Sci, 2001. 8(2): p. 197-205.
96. Hamburgh, M. E., W. C. Drosopoulos, and V. R. Prasad, *The influence of 3TC-resistance mutations E89G and M184V in the human immunodeficiency virus reverse transcriptase on mispair extension efficiency.* Nucleic Acids Res, 1998. 26(19): p. 4389-94.
97. Garforth, S. J., et al., *Site-directed mutagenesis in the fingers subdomain of HIV-1 reverse transcriptase reveals a specific role for the beta3-beta4 hairpin loop in dNTP selection.* J Mol Biol, 2007. 365(1): p. 38-49.
98. Meyer, P. R., et al., *A mechanism of AZT resistance: an increase in nucleotide-dependent primer unblocking by mutant HIV-1 reverse transcriptase.* Mol Cell, 1999. 4(1): p. 35-43.
99. Meyer, P. R., et al., *Differential removal of thymidine nucleotide analogues from blocked DNA chains by human immunodeficiency virus reverse transcriptase in the presence of physiological concentrations of 2'-deoxynucleoside triphosphates.* Antimicrob Agents Chemother, 2000. 44(12): p. 3465-72.
100. Meyer, P. R., et al., *Effects of specific zidovudine resistance mutations and substrate structure on nucleotide-dependent primer unblocking by human immunodeficiency virus type 1 reverse transcriptase.* Antimicrob Agents Chemother, 2002. 46(5): p. 1540-5.
101. Gerondelis, P., et al., *The P236L delavirdine-resistant human immunodeficiency virus type 1 mutant is replication defective and demonstrates alterations in both RNA 5'-end-and DNA 3'-end-directed RNase H activities.* J Virol, 1999. 73(7): p. 5803-13.
102. Johnson, A. A., et al., *Human mitochondrial DNA polymerase holoenzyme: reconstitution and characterization.* Biochemistry, 2000. 39(7): p. 1702-8.
103. Anderson, K. S. and K. A. Johnson, *Kinetic and structural analysis of enzyme intermediates: lessons from EPSP synthase.* Chem. Rev., 1990. 90: p. 1131-1149.
104. Vaccaro, J. A., et al., *Mechanism of inhibition of Human Immunodeficiency Virus Type 1 Reverse Transcriptase by d4TTP: an equivalent invorporation efficiency relative to the natrual substrate dTTP.* Antimicrob Agents Chemother, 2000. 44: p. 217-21.
105. Ray, A. S. and K. S. Anderson, *Mechanistic studies to understand the inhibition of wild type and mutant HIV-1 reverse transcriptase by Carbovir-triphosphate.* Nucleosides Nucleotides Nucleic Acids, 2001. 20(4-7): p. 1247-50.
106. Ray, A. S., et al., *Interaction of 2'-deoxyguanosine triphosphate analogue inhibitors of HIV reverse transcriptase with human mitochondrial DNA polymerase gamma.* Antivir Chem Chemother, 2007. 18(1): p. 25-33.
107. Chu, C. K., et al., *Comparative activity of 2',3'-saturated and unsaturated pyrimidine and purine nucleosides* against human immunodeficiency virus type 1 in peripheral blood mononuclear cells. Biochem Pharmacol, 1988. 37(19): p. 3543-8.
108. Ray, A. S., et al., Novel use of a guanosine prodrug approach to convert 2',3'-didehydro-2',3'-dideoxyguanosine into a viable antiviral agent. Antimicrob Agents Chemother, 2002. 46(3): p. 887-91.
109. Ray, A. S., et al., Mechanism of anti-human immunodeficiency virus activity of beta-D-6-cyclopropylamino-2',3'-didehydro-2',3'-dideoxyguanosine. Antimicrob Agents Chemother, 2005. 49(5): p. 1994-2001.
110. Dutschman, G. E., et al., Novel 4'-substituted stavudine analog with improved anti-human immunodeficiency virus activity and decreased cytotoxicity. Antimicrob Agents Chemother, 2004. 48(5): p. 1640-6.
111. Haraguchi, K., et al., Synthesis of a highly active new anti-HIV agent 2',3'-didehydro-3'-deoxy-4'-ethynylthymidine. Bioorg Med Chem Lett, 2003. 13(21): p. 3775-7.
112. Kodama, E. I., et al., 4'-Ethynyl nucleoside analogs: potent inhibitors of multidrug-resistant human immunodeficiency virus variants in vitro. Antimicrob Agents Chemother, 2001: p. 1539-46.
113. Ohrui, H., et al., Syntheses of 4'-C-ethynyl-beta-D-arabino- and 4'-C-ethynyl-2'-deoxy-beta-D-ribo-pentofuranosylpyrimidines and-purines and evaluation of their anti-HIV activity. J Med Chem, 2000. 43(23): p. 4516-25.
114. Hsu, C. H., et al., Comparison of the phosphorylation of 4'-ethynyl 2',3'-dihydro-3'-deoxythymidine with that of other anti-human immunodeficiency virus thymidine analogs. Antimicrob Agents Chemother, 2007. 51(5): p. 1687-93.
115. Paintsil, E., et al., Intracellular Metabolism and Persistence of the Anti-Human Immunodeficiency Virus Activity of 2',3'-Didehydro-3'-Deoxy-4'-Ethynylthymidine, A Novel Thymidine Analog. Antimicrob Agents Chemother, 2007.
116. Nakata, H., et al., Antiviral Activity Against HIV-1, Intracellular Metabolism, and Effects on Human DNA Polymerases of 4'Ethynlyl-2-fluoro-2'deoxyadenosine. Antimicrobial Agents and Chemotherapy, In Revision, 2007. In press.
117. Highleyman, L., Lodenosine trials stopped due to safety concerns. Beta, 1999. 12(4): p. 4.
118. Jochmans, D., et al., Indolopyridones inhibit human immunodeficiency virus reverse transcriptase with a novel mechanism of action. J Virol, 2006. 80(24): p. 12283-92.
119. Anderson, J. P., R. Daifuku, and L. A. Loeb, Viral error catastrophe by mutagenic nucleosides. Annu Rev Microbiol, 2004. 58: p. 183-205.
120. Daifuku, R., Stealth nucleosides: mode of action and potential use in the treatment of viral diseases. BioDrugs, 2003. 17(3): p. 169-77.
121. Harris, K., et al., SN1212/1461: a novel deoxyribonucleoside analog with activity against HIV. CROI 2004. abstract no. 532.
122. Harris, K. S., et al., KP-1212/1461, a nucleoside designed for the treatment of HIV by viral mutagenesis. Antiviral Res, 2005. 67(1): p. 1-9.
123. Murakami, E., et al., Mechanism of action of a novel viral mutagenic covert nucleotide: molecular interactions with HIV-1 reverse transcriptase and host cell DNA polymerases. Antiviral Res, 2005. 67(1): p. 10-7.
124. Hirsch, M. S., Entecavir surprise. N Engl J Med, 2007. 356(25): p. 2641-3.
125. McMahon, M. A., et al., The Hepatitis B Drug Entecavir Inhibits HIV Replication and Can Lead to Resistant HIV. New England Journal of Medicine, 2007. In Press.
126. Levine, S., et al., Efficacies of entecavir against lamivudine-resistant hepatitis B virus replication and recombinant polymerases in vitro. Antimicrob Agents Chemother, 2002. 46(8): p. 2525-32.
127. Innaimo, S. F., et al., Identification of BMS-200475 as a potent and selective inhibitor of hepatitis B virus. Antimicrob Agents Chemother, 1997. 41(7): p. 1444-8.
128. Yamanaka, G., et al., Metabolic studies on BMS-200475, a new antiviral compound active against hepatitis B virus. Antimicrob Agents Chemother, 1999. 43(1): p. 190-3.
129. Marion, P. L., et al., Potent efficacy of entecavir (BMS-200475) in a duck model of hepatitis B virus replication. Antimicrob Agents Chemother, 2002. 46(1): p. 82-8.
130. Vaccaro, J. A. and K. S. Anderson, Implication of the tRNA initiation step for human immunodeficiency virus type 1 reverse transcriptase in the mechanism of 3'-azido-3'-deoxythymidine (AZT) resistance. Biochemistry, 1998. 37(40): p. 14189-14194.
131. Vaccaro, J. A., H. A. Singh, and K. S. Anderson, Initiation of minus-strand DNA synthesis by human immunodeficiency virus type 1 reverse transcriptase. Biochemistry, 1999. 38(48): p. 15978-85.
132. Wang, P., et al., Recent advances in L-nucleosides: chemistry and biology. Antiviral Res., 1998. 40: p. 19-44.
133. Dutschman, G. E., et al., Metabolism of 2',3'-dideoxy-2',3'didehydro-b-L (−)-5-fluorocytidine and its activity in combination with clinically approved anti-human imunodeficiency virus b-D(+) nucleoside analogs in vitro. Antimicrob. Agents Chemother., 1998. 42: p. 1799-1804.
134. Hurwitz, S. J., et al., Pharmacodynamics of (−)-b-2',3'-dideoxy-3'-thiacytidine in chronically virus-infected woodchucks compared to its pharmacodynamics in humans. Antimicrob. Agents Chemother., 1998. 42: p. 2804-2809.
135. Shi, J., et al., Synthesis and biological evaluation of 2',3'-didehydro-2',3'-dideoxy-5-fluorocytidine (D4FC) analogues: Discovery of carbocyclic nucleoside triphosphates with potent inhibitory activity against HIV-1 reverse transcriptase. J. Med. Chem., 1999. 42: p. 859-867.
136. Kim, H. O., et al., L-beta-(2S, 4S)- and L-alpha-(2S, 4R)-dioxolanyl nucleosides as potential anti-HIV agents: asymmetric synthesis and structure-activity relationships. J Med Chem, 1993. 36(5): p. 519-28.
137. Feng, J. Y., et al., Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother, 2004. 48(4): p. 1300-6.
138. Ray, A. S., et al., Interactions of enantiomers of 2',3'-didehydro-2',3'-dideoxy-fluorocytidine with wild type and M184V mutant HIV-1 reverse transcriptase. Antiviral Res, 2002. 56(3): p. 189-205.
139. Murakami, E., et al., Investigating the effects of stereochemistry on incorporation and removal of 5-fluorocytidine analogs by mitochondrial DNA polymerase gamma: comparison of D- and L-D4FC-TP. Antiviral Res, 2004. 62(1): p. 57-64.
140. Ray, A. S., et al., Probing the mechanistic consequences of 5-fluorine substitution on cytidine nucleotide analogue incorporation by HIV-1 reverse transcriptase. Antivir Chem Chemother, 2003. 14(3): p. 115-25.
141. Shi, J., et al., 2('),3(')-didehydro-2('),3(')-dideoxynucleosides are degraded to furfuryl alcohol under acidic conditions. Bioorg Med Chem Lett, 2004. 14(9): p. 2159-62.

142. Kosalaraksa, P., et al., *Comparative fitness of multi-dideoxynucleoside-resistant human immunodeficiency virus type 1 (HIV-1) in an In vitro competitive HIV-1 replication assay.* J Virol, 1999. 73(7): p. 5356-63.

143. Deval, J., et al., *The molecular mechanism of multidrug resistance by the Q151M human immunodeficiency virus type 1 reverse transcriptase and its suppression using alpha-boranophosphate nucleotide analogues.* J Biol Chem, 2002. 277(44): p. 42097-104.

144. Lee, H. R. and K. A. Johnson, *Fidelity and processivity of reverse transcription by the human mitochondrial DNA polymerase.* J Biol Chem, 2007.

145. Murakami, E., et al., *Characterization of a novel reverse transcriptase and other RNA associated catalytic activities by human DNA polymerase gamma: Importance in mitochondrial DNA replicationn.* J Biol Chem, 2003.

146. Basavapathruni, A., C. M. Bailey, and K. S. Anderson, *Defining a molecular mechanism of synergy between nucleoside and nonnucleoside AIDS drugs.* J Biol Chem, 2004. 279(8): p. 6221-4.

147. Basavapathruni, A., et al., *Modulation of human immunodeficiency virus type 1 synergistic inhibition by reverse transcriptase mutations.* Biochemistry, 2006. 45(23): p. 7334-40.

148. Basavapathruni, A. and K. S. Anderson, *Developing novel nonnucleoside HIV-1 reverse transcriptase inhibitors: beyond the butterfly.* Curr Pharm Des, 2006. 12(15): p. 1857-65.

149. Odriozola, L., et al., *Nonnucleoside inhibitors of HIV-1 reverse transcriptase inhibit phosphorolysis and resensitize the 3'-azido-3'-deoxythymidine (AZT)-resistant polymerase to AZTTP.* J Biol Chem, 2003.

150. Maga, G., et al., *Potentiation of inhibition of wild-type and mutant human immunodeficiency virus type 1 reverse transcriptases by combinations of nonnucleoside inhibitors and d-and L-(beta)-dideoxynucleoside triphosphate analogs.* Antimicrobial Agents & Chemotherapy., 2001. 45(4): p. 1192-200.

151. Jencks, W. P., *On the attribution and additivity of binding energies.* Proc Natl Acad Sci USA, 1981. 78(7): p. 4046-4050.

152. Hajduk, P. J., R. P. Meadows, and S. W. Fesik, *Discovering high-affinity ligands for proteins.* Science, 1997. 278: p. 497-499.

153. Shuker, S., et al., *Discovering high-affinity ligands for proteins: SAR by NMR.* Science, 1996. 274: p. 1531-1534.

154. Gavriliu, D., et al., *Synthesis and anti-HIV activity of [d4U]-[trovirdine analogue] and [d4T]-[trovirdine analogue] heterodimers as inhibitors of HIV-1 reverse transcriptase.* Nucleosides Nucleotides Nucleic Acids, 2002. 21(8-9): p. 505-33.

155. Gavriliu, D., et al., *Synthesis and antiviral activity of C-5 substituted analogues of d4T bearing methylamino-or methyldiamino-linker arms.* Nucleosides Nucleotides Nucleic Acids, 2000. 19(5-6): p. 1017-31.

156. Laduree, D., et al., *Synthesis of novel C-5 substituted d4T analogues bearing linker arms as potential anti-HIV agents.* Nucleosides Nucleotides, 1999. 18(4-5): p. 883-4.

157. Renoud-Grappin, M., et al., *Imidazo (1,5-b)pyridazine-d4t conjugates: synthesis and anti-human immunodeficiency virus evaluation.* Antiviral Chem. Chemother., 1998. 9: p. 205-223.

158. Velazquez, S., et al., *Synthesis and anti-HIV activity of [AZT]-[TSAO-T] and [AZT]-[HEFT] dimers as potential multifunctional inhibitors of HIV-1 reverse transcriptase.* J Med Chem, 1995. 38(10): p. 1641-9.

159. Velazquez, S., et al., *Hybrids of [TSAO-T]-[foscarnet]: The first conjugate of foscarnet with a non-nucleoside reverse transcriptase inhibitor through a labile covalent ester bond.* J Med Chem, 2004. 47(13): p. 3418-26.

160. Velazquez, S., et al., *Novel series of [ddN]-[TSAO-T] heterodimers as potential bi-functional inhibitors of HIV-1 RT Studies in the linker and ddN region.* Nucleosides Nucleotides, 1999. 18(4-5): p. 1029-30.

161. Nanni, R. G., et al., Perspectives in Drug Discovery, 1993. 1: p. 129.

162. Mao, C., et al., *Structure-based design of non-nucleoside reverse transcriptase inhibitors of drug-resistant human immunodeficiency virus.* Antivir Chem Chemother, 1999. 10(5): p. 233-40.

163. Ruth, J. L. and Y. Cheng, *Selective antiviral agents. The metabolism of 5-propyl-2'-deoxyuridine and effects on DNA synthesis in herpes simplex virus type 1 infections.* J Biol Chem, 1982. 257(17): p. 10261-6.

164. Chen, B.-C., et al., *5'-Benzoyl-2'a-bromo-3'-O-methanesulfonylthymidine: a superior nucleoside for the synthesis of the anti-AIDS drug D4T (stavudine).* Tetrahedron Letters, 1995. 36(44): p. 7957-60.

165. Hunter, R., et al., *[d4U]-butyne-[HI-236] as a non-cleavable, bifunctional NRTI/NNRTI HIV-1 reverse-transcriptase inhibitor.* Bioorg Med Chem Lett, 2007. 17(9): p. 2614-7.

166. Sugeac, E., et al., *Synthesis and anti-HIV activity of some heterodimers [NRTI]-glycyl-succinyl-[trovirdine analogue] of known HIV-1 reverse transcriptase inhibitors.* J Enzyme Inhib Med Chem, 2003. 18(2): p. 175-86.

167. Langley, D. R., et al., *Inhibition of hepatitis B virus polymerase by entecavir.* J Virol, 2007. 81(8): p. 3992-4001.

168. Seifer, M., et al., *In vitro inhibition of hepadnavirus polymerases by the triphosphates of BMS-200475 and lobucavir.* Antimicrob Agents Chemother, 1998. 42(12): p. 3200-8.

169. Chen, M. S., et al., *Selective action of 4'-azidothymidine tri phosphate on reverse transcriptase of human immunodeficiency virus type 1 and human DNA polymerases alpha and beta.* Biochemistry, 1993. 32(23): p. 6002-10.

170. Jorgensen, W. L., et al., *Computer-aided design of non-nucleoside inhibitors of HIV-1 reverse transcriptase.* Bioorg Med Chem Lett, 2006. 16(3): p. 663-7.

171. Ruiz-Caro, J., et al., *Optimization of diarylamines as non-nucleoside inhibitors of HIV-1 reverse transcriptase.* Bioorg Med Chem Lett, 2006. 16(3): p. 668-71.

172. Kim, J. T., et al., *FEP-guided selection of bicyclic heterocycles in lead optimization for non-nucleoside inhibitors of HIV-1 reverse transcriptase.* J Am Chem Soc, 2006. 128(48): p. 15372-3.

173. Thakur, V. V., et al., *Optimization of pyrimidinyl-and triazinyl-amines as non-nucleoside inhibitors of HIV-1 reverse transcriptase.* Bioorg Med Chem Lett, 2006. 16(21): p. 5664-7.

174. Mhiri, C., et al., *Zidovudine myopathy: a distinctive disorder associated with mitochondrial dysfunction.* Annals. of. Neurology., 1991. 29: p. 606-614.

175. Parker, W. B. and Y.-C. Cheng, *Mitochondrial toxicity of antiviral nucleoside analogs.* J. NIH. Res., 1994. 6: p. 57-61.

176. Yang, G., et al., *Highly selective action of triphosphate metabolite of 4'-ethynyl D4T: a novel anti-HIV compound against HIV-1 RT.* Antiviral Res, 2007. 73(3): p. 185-91.

177. Nitanda, T., et al., *Anti-human immunodeficiency virus type 1 activity and resistance profile of 2',3'-didehydro-3'-*

178. Lewis, W., *Pharmacogenomics, Toxicogenomics, and DNA Polymerase gamma.* J Infect Dis, 2007. 195(10): p. 1399-401.

179. Luzhansky, J. Z., et al., *Leber's hereditary optic neuropathy in the setting of nucleoside analogue toxicity.* Aids, 2001. 15(12): p. 1588-9.

180. Yamanaka, H., et al., *Novel Mutation of Human DNA Polymerase gamma Associated with Mitochondrial Toxicity Induced by Anti-HIV Treatment.* J Infect Dis, 2007. 195(10): p. 1419-25.

181. Pata, J. D., et al., *Structure of HIV-1 reverse transcriptase bound to an inhibitor active against mutant reverse transcriptases resistant to other nonnucleoside inhibitors.* Proc Natl Acad Sci USA, 2004. 101(29): p. 10548-53.

182. Spence, R. A., K. S. Anderson, and K. A. Johnson, *HIV-1 reverse transcriptase resistance to nonnucleoside inhibitors.* Biochemistry, 1996. 35(3): p. 1054-63.

183. Folta-Stogniew, E., et al., *Exchange of DNA base pairs that coincides with recognition of homology promoted by E. coli RecA protein.* Mol Cell, 2004. 15(6): p. 965-75.

184. Shah, A. M., et al., *Y265H mutator mutant of DNA polymerase beta. Proper teometric alignment is critical for fidelity.* J Biol Chem, 2001. 276(14): p. 10824-31.

185. Pelemans, H., et al., *Mutations at amino acid positions 63, 189, and 396 of human immunodeficiency virus type 1 reverse transcriptase (RT) partially restore the DNA polymerase activity of a Trp229Tyr mutant RT.* Virology, 2001. 287(1): p. 143-50.

186. Wisniewski, M., et al., *Mutations in the primer grip region of HIV reverse transcriptase can increase replication fidelity.* J Biol Chem, 1999. 274(40): p. 28175-84.

187. Wohrl, B. M., et al., *Kinetic analysis of four HIV-1 reverse transcriptase enzymes mutated in the primer grip region of p66. Implications for DNA synthesis and dimerization.* J Biol Chem, 1997. 272(28): p. 17581-7.

188. Pelemans, H., et al., *Mutational analysis of trp-229 of human immunodeficiency virus type 1 reverse transcriptase (RT) identifies this amino acid residue as a prime target for the rational design of new non-nucleoside RT inhibitors.* Mol Pharmacol, 2000. 57(5): p. 954-60.

189. Ren, J., et al., *Crystal structures of HIV-1 reverse transcriptase in complex with carboxanilide derivatives.* Biochemistry, 1998. 37(41): p. 14394-403.

190. Myrick, F., et al., *The Triple Combination of Tenofovir, Emtricitabine, and Efavirenz Shows Synergistic Anti-HIV-1 Activity In Vitro.* Antiviral Research, 2007. 74: p. Abstract #83 page A61.

191. Tirado-Rives, J. and W. L. Jorgensen, *Contribution of conformer focusing to the uncertainty in predicting free energies for protein-ligand binding.* J Med Chem, 2006. 49(20): p. 5880-4.

192. Greenwald, R. B., *PEG drugs: an overview.* J Control Release, 2001. 74(1-3): p. 159-71.

193. Bettio, F., et al., *Synthesis and Biological In Vitro Evaluation of Novel PEG-Psoralen Conjugates.* Biomacromolecules, 2006. 7(12): p. 3534-3541.

194. Greenwald, R. B., et al., *A new aliphatic amino prodrug system for the delivery of small molecules and proteins utilizing novel PEG derivatives.* J Med Chem, 2004. 47(3): p. 726-34.

195. Manetsch, R., et al., *In Situ Click Chemistry: Enzyme Inhibitors Made to Their Own Specifications.* Journal of the American Chemical Society, 2004. 126(40): p. 12809-12818.

196. Silverman, A. P. and E. T. Kool, *RNA Probes of Steric Effects in Active Sites: High Flexibility of HIV-1 Reverse Transcriptase.* J Am Chem Soc, 2007. 129(35): p. 10626-7.

197. Das, K., et al., *Crystal structures of clinically relevant Lys103Asn/Tyr181Cys double mutant HIV-1 reverse transcriptase in complexes with ATP and non-nucleoside inhibitor HBY 097.* J Mol Biol, 2007. 365(1): p. 77-89.

198. Kukhanova, M., et al., *Design of anti-HIV compounds: from nucleoside to nucleoside 5'-triphosphate analogs. Problems and perspectives.* Current Pharmaceutical Design, 2000. 6(5): p. 585-98.

199. McGuigan, C., et al., *Aryl phosphoramidate derivatives of d4T have improved anti-HIV efficacy in tissue culture and may act by the generation of a novel intracellular metabolite.* J Med Chem, 1996. 39(8): p. 1748-53.

200. Camp, R., *Antiretrovirals in Development Pipeline 2007.* Pipeline Report, 2007.

201. McGuigan, C., et al., *Certain phosphoramidate derivatives of dideoxy uridine (ddU) are active against HIV and successfully by-pass thymidine kinase.* FEBS Lett, 1994. 351(1): p. 11-4.

202. Mehellou, Y., et al., *Design, synthesis, and anti-HIV activity of 2',3'-didehydro-2',3'-dideoxyuridine (d4U), 2',3'-dideoxyuridine (ddU) phosphoramidate 'ProTide' derivatives.* Bioorg Med Chem Lett, 2007. 17(13): p. 3666-9.

203. Lee, W. A. and J. C. Martin, *Perspectives on the development of acyclic nucleotide analogs as antiviral drugs.* Antiviral Res, 2006. 71(2-3): p. 254-9.

204. Robbins, B. L., et al., *Metabolic pathways for activation of the antiviral agent 9-(2-phosphonylmethoxyethyl)adenine in human lymphoid cells.* Antimicrob Agents Chemother, 1995. 39(10): p. 2304-8.

205. Srinivas, R. V., et al., *Metabolism and in vitro antiretroviral activities of bis(pivaloyloxymethyl) prodrugs of acyclic nucleoside phosphonates.* Antimicrob Agents Chemother, 1993. 37(10): p. 2247-50.

206. Udier-Blagovic, M., J. Tirado-Rives, and W. L. Jorgensen, *Validation of a model for the complex of HIV-1 reverse transcriptase with nonnucleoside inhibitor TMC125.* J Am Chem Soc, 2003. 125(20): p. 6016-7.

207. Ray, A. S., et al., *Insights into the molecular mechanism of inhibition and drug resistance for HIV-1 RT with carbovir triphosphate.* Biochemistry, 2002. 41(16): p. 5150-62.

208. Hill, A., et al., *Modelling-based prediction of clinical benefits from etravirine in the TMC125-C223 trial.* HIV Clin Trials, 2007. 8(2): p. 68-76.

209. Temesgen, Z., *The latest in antiretroviral therapy.* Drug News Perspect, 2006. 19(8): p. 491-8.

210. Janssen, P. A., et al., *In search of a novel anti-HIV drug: multidisciplinary coordination in the discovery of 4-[[4-[[4-[(1E)-2-cyanoethenyl]-2,6-dimethylphenyl]amino]-2-pyrimidinyl]amino]benzonitrile (R278474, rilpivirine).* J Med Chem, 2005. 48(6): p. 1901-9.

211. Katritzky, A. R., et al., *The tautomeric equilibria of thio analogs of nucleic acid bases. Part 1. 2-Thiouracil: background, preparation of model compounds, and gas-phase proton affinities.* Journal of the Chemical Society, Perkin Transactions 2: Physical Organic Chemistry (1972-1999), 1989(10): p. 1499-506.

212. Spychala, J., *A convenient synthesis of monocationic 1-[(cyclic amidino)methyl]thymines.* Synthetic Communications, 1997. 27(19): p. 3431-3440.

213. Zhang, Y.-M., T. Razler, and P. F. Jackson, *Synthesis of pyrimido[4,5-b]indoles and benzo[4,5]furo[2,3-d]pyrimidines via palladium-catalyzed intramolecular arylation.* Tetrahedron Letters, 2002. 43(46): p. 8235-8239.

214. Arnott, G., et al., *New methodology for 2-alkylation of 3-furoic acids: application to the synthesis of tethered UC-781/d4T bifunctional HIV reverse-transcriptase inhibitors.* Tetrahedron Letters, 2005. 46(23): p. 4023-4026.
215. Ciurea, A., et al., *Synthesis of 5-alkynylated d4T analogues as potential HIV-1 reverse transcriptase inhibitors.* J Enzyme Inhib Med Chem, 2004. 19(6): p. 511-9.
216. Hernandez, E., et al., *Synthesis of a series of symmetrically disubstituted diacetylenes with polychlorophenyl rings as side groups and linear polyether chains as spacers.* Synthesis, 1992(11): p. 1164-9.
217. Capek, P., R. Pohl, and M. Hocek, *Cross-coupling reactions of unprotected halopurine bases, nucleosides, nucleotides and nucleoside triphosphates with 4-boronophenylalanine in water. Synthesis of (purin-8-yl)- and (purin-6-yl)phenylalanines.* Organic & Biomolecular Chemistry, 2006. 4(11): p. 2278-2284.
218. Lang, P., et al., *Synthesis of 8-(omega-Hydroxyalkyl)-, 8-(omega-Hydroxyalk-1-enyl)-, and 8-(omega-Hydroxyalk-1-ynyl)adenines Using the tert-Butyldimethylsilyloxymethyl Group, a New and Versatile Protecting Group of Adenine.* J. Org. Chem., 2000. 65(23): p. 7825-7832.
219. Kesteleyn, B. R. R., et al., *Preparation of substituted pyrido[3,2-b]indoles for use in pharmaceutical compositions for the treatment of HIV-infection.* 2004, (Tibotec Pharmaceuticals Ltd., Ire.). Patent #: WO2004046143 p. 91.
220. Meyer, P. R., et al., *Chain-terminating dinucleoside tetraphosphates are substrates for DNA polymerization by human immunodeficiency virus type 1 reverse transcriptase with increased activity against thymidine analogue-resistant mutants.* Antimicrob Agents Chemother, 2006. 50(11): p. 3607-14.
221. Dharmasena, S., et al., *3'-Azido-3'-deoxythymidine-(5)-tetraphospho-(5')-adenosine, the product of ATP-mediated excision of chain-terminating AZTMP, is a potent chain-terminating substrate for HIV-1 reverse transcriptase.* Biochemistry, 2007. 46(3): p. 828-36.

The invention claimed is:
1. A compound according to the chemical structure:

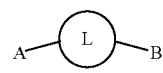

Where A is a nucleoside reverse transcriptase inhibitor (NRTI) compound or a nucleoside competitive reverse transcriptase inhibitor (NCRIT) compound modified to form a chemical bond with said linker group

without significant loss of HIV-1 reverse transcriptase inhibitory activity, B is a non-nucleoside reverse transcriptase inhibitor compound modified to bond to said linker group

without significant loss of HIV-1 reverse transcriptase inhibitory activity and said linker

is a linker group according to the chemical structure:

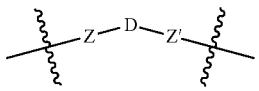

Where Z and Z' are each independently a bond, —(CH$_2$)$_i$—O, —(CH$_2$)$_i$—S, —(CH$_2$)$_i$—N—R,

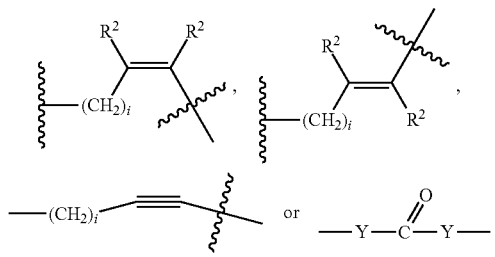

wherein said —(CH$_2$)$_i$ group, if present in Z or Z', is bonded to A or B;
each R is independently H, or a C$_1$-C$_3$ alkyl or alkanol group;
Each R$^2$ is independently H or a C$_1$-C$_3$ alkyl group;
Each Y is independently a bond, O, S or N—R;
Each i is independently 0, 1, 2 or 3;
D is

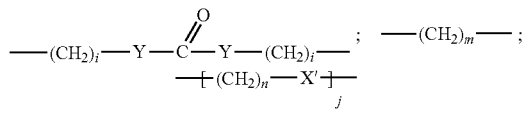

or
a bond, with the proviso that Z, Z' and D are not each simultaneously bonds;
j is 1, 2, 3 or 4,
m is 1, 2, 3, 4, 5 or 6;
n is 1, 2 or 3; and
X' is O, S or N—R
or a pharmaceutically acceptable salt thereof.

2. The compound according to claim 1 wherein said nucleoside reverse transcriptase inhibitor is selected from the group consisting of zidovudine (AZT), lamivudine (3TC), emtricitabine (FTC), abacavir (ABC), stavudine (d4T), didanosine (ddI), dideoxycytidine (ddC), amdoxovir (DAPD), apricitabine (ATC), elvucitabine (B-LFd4C), tenofovir ((9-[9(R)-2-(phosphonomethoxy)propyl]adenine or PMPA) or tenofovir prodrug (tenofovir disoproxil fumarate-9-[(R)-2-[[bis[[(isopropoxycarbonyl)oxy]-methoxy]phosphinyl]methoxy]propyl]adenine fumarate), 4'-ethynyl D4T (4'ED4T), 4'-ethynyl-2-fluoro-2'-deoxyadeonsine (4'EFdA), entecavir and Racivir (racemic mixture of ±FTC).

3. The compound according to claim 1 or 2 wherein the non-nucleoside reverse transcriptase inhibitor is selected from the group consisting of nevirapine, delavirdine, efavirenz, TIBO, UC-781 and TMC 125.

4. The compound according to claim 1 or 2 wherein the non-nucleoside reverse transcriptase inhibitor is selected from the group consisting of nevirapine (BI-R6-587), delavirdine (U-90152S/T), efavirenz (DMP-266), UC-781 (N-[4-chloro-3-(3-methyl-2-butenyloxy)phenyl]-2-methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4''-dimethoxy-5',5''-bis(methoxycarbonyl)-6,6-diphenylhexenoate), 3-Bromo-5-(1-5-bromo-4-methoxy-3-((Adam analog) 5Cl3PhS-2IndolCONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyl)-)carbonyl]-4-[3-(isopropylamino)-2-pyridinyl]piperazine (piperazine 1pyridine 4 indolyl derivative), 1-[5-[[N-(methyl)methylsulfonylamino]-2-indolylcarbonyl-4-[3-(isopropylamino)-2-pyridinyl]piperazine (piperazine 1pyridine 5 indolyl derivative), 1-[3-(Ethylamino)-2-[pyridinyl]-4-[(5-hydroxy-2-indolyl)carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A_(NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS,
E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-2-(5-methylpyridyl)Thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl) thiourea, N-(2-Phenethyl)-N'-(2-thiazolyl)thiourea (LY-73497), L-697,639, L-697,593, L-697,661, 3-[2-(4, 7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl] amine]-5-ethyl-6-methyl(pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38, UC-781 and UC-84.

5. The compound according to claim 1 wherein said NRTI comprises a pyrimidine base and said NRTI is covalently bonded to the linker at the 5 position of said pyrimidine base.

6. The compound according to claim 1 wherein said NRTI comprises a purine base and said NRTI is covalently bonded to the linker at the C-7 position of said purine base.

7. The compound according to claim 1 wherein said NNRTI is covalently linked to the linker at a position on the NNRTI molecule which is a para or meta position of a phenyl group on wing-2 or at an atom which is furthermost disposed off of the wing-2 portion of the molecule toward the NRTI active site when the NNRTI molecule is bound to its site in the reverse transcriptase.

9. The compound according to claim 8 according to the chemical structure:

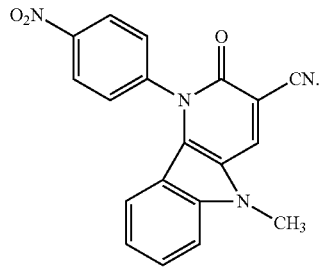

10. The compound according to claim 8 linked to said linker group at a distal carbon position (furthest from the nitrogen) on the phenyl group of the indole moiety.

11. A compound according to the chemical structure:

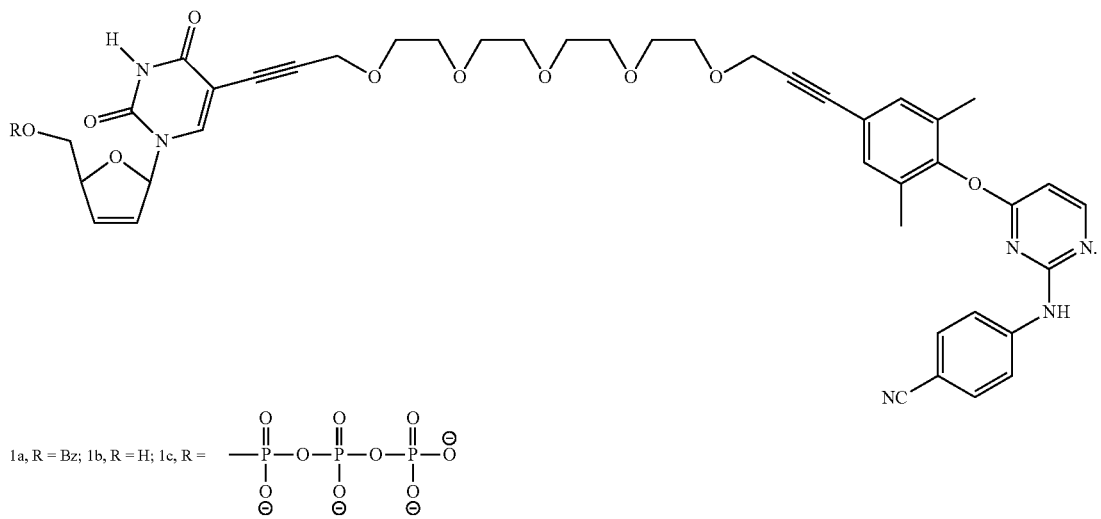

8. The compound according to claim 1 wherein said NCRTI is a compound according to the chemical structure:

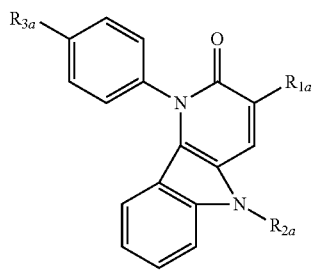

Where $R_{3a}$ is CN or $NO_2$;
$R_{1a}$ is cyano, nitro, methyloxycarbonyl, methylaminocarbonyl, ethyloxycarbonyl or ethylaminocarbonyl; and
$R_{2a}$ is H or a $C_1$-$C_4$ alkyl group which may be optionally substituted with a hydroxyl group or is a bond linking a linker to said NNRTI.

12. A compound according to claim 1 as set forth in FIG. 5.
13. A compound according to claim 1 as set forth in FIG. 6.
14. A compound according to claim 1 as set forth in FIG. 8.
15. A compound according to claim 1 wherein a free hydroxyl group on the sugar synthon of the NRTI is optionally substituted with an acyl group, a $C_1$-$C_{20}$ alkyl or ether group, an amino acid residue (D or L), a phosphate, diphosphate, triphosphate or phosphodiester group.
16. The compound according to claim 1 wherein said NRTI compound contains a cytosine, adenine or guanine base.
17. The compound according to claim 16 wherein the exocyclic amine of the cytosine, adenine or guanine base is optionally substituted with an acyl group, a $C_1$-$C_{20}$ alkyl group or ether group or an amino acid residue (D or L).
18. A pharmaceutical composition comprising an effective amount of a compound according to claim 1, optionally in combination with a pharmaceutically acceptable carrier, additive or excipient.
19. The composition according to claim 18 adapted for oral administration.
20. The composition according to claim 18 adapted for parenteral administration.
21. The composition according to claim 18 adapted for administration via an intravenous route.

22. The pharmaceutical composition according to claim 18 further comprising an effective amount of an HIV integrase inhibitor, an HIV protease inhibitor, an HIV fusion inhibitor or mixtures thereof.

23. The composition according to claim 22 wherein said HIV integrase inhibitor is raltegravir, elvitegravir or mixtures thereof.

24. The composition according to claim 22 wherein said HIV protease inhibitor is saquinavir, ritonavir or mixtures thereof.

25. The composition according to claim 22 wherein said HIV fusion inhibitor is maraviroc, enfuvirtide, vicriviroc, aplaviroc, TNS-355, PRO140, BMS-488043 or mixtures thereof.

26. A method of inhibiting HIV-1 reverse transcriptase in a patient in need thereof comprising administering an effective amount of a composition according to claim 18 to said patient.

27. A method of treating an HIV infection in a patient in need thereof, said method comprising administering to said patient an effective amount of a composition according to claim 18 to said patient.

28. A method of reducing the likelihood of an HIV infection in a patient at risk for said infection, said method comprising administering to said patient an effective amount of a composition according to claim 18 to said patient.

29. A method of treating a patient with AIDS or ARC comprising administering to said patient a therapeutically effective amount of a composition according to claim 18.

30. A method of reducing the likelihood that an HIV infection in a patient will worsen to AIDS or ARC comprising administration to a patient in need thereof an effective amount of a composition according to claim 18.

31. The method according to claim 26 wherein said infection or condition is caused by a drug resistant strain of HIV.

32. The method according to claim 26 wherein said reverse transcriptase is from a drug resistant strain of HIV.

33. The method according to claim 30 wherein said drug resistant strain of HIV is selected from the group consisting of XXBRU, K65R, Y115F, F116Y, Q151M, M184V, L74V, V75T, 4XZT, T215Y, K103N, T215Y/M184V, 5705-72, 488-101, C910-6, LA1M184V, 0910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I and Y188C/H.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: synthetic primer

<400> SEQUENCE: 1
tcaggtccct gttcgggcgc cac                                    23

<210> SEQ ID NO 2
<211> LENGTH: 24
<212> TYPE: DNA
<213> ORGANISM: Artificial Sequence
<220> FEATURE:
<223> OTHER INFORMATION: synthetic primer

<400> SEQUENCE: 2
tcaggtccct gttcgggcgc cact                                   24

<210> SEQ ID NO 3
<211> LENGTH: 36
<212> TYPE: DNA
<213> ORGANISM: Artificial Sequence
<220> FEATURE:
<223> OTHER INFORMATION: synthetic template

<400> SEQUENCE: 3
tctctagcag tggcgcccga acagggacct gaaagc                      36